(12) United States Patent
Dekany et al.

(10) Patent No.: US 8,802,841 B2
(45) Date of Patent: Aug. 12, 2014

(54) 1,2-DIDEOXY-1,2-DIAMINO OLIGOSACCHARIDES AND POLYSACCHARIDES AND DERIVATIVES THEREOF

(75) Inventors: Gyula Dekany, Sinnamon Park (AU); István Bajza, Debrecen (HU); Marie Bøjstrup, Tåstrup (DK); Károly Ágoston, Telki (HU); Lars Kröger, Hamburg (DE); Ignacio Figueroa Pérez, Copenhagen (DK); Christoph H. Röhrig, Mühlingen (DE); Paulo Vital, København V (DK); Erzsébet Czinege, Esztergom (HU)

(73) Assignee: Glycom A/S, Kgs. Lyngby (DK)

( * ) Notice: Subject to any disclaimer, the term of this patent is extended or adjusted under 35 U.S.C. 154(b) by 336 days.

(21) Appl. No.: 12/741,973

(22) PCT Filed: Nov. 3, 2008

(86) PCT No.: PCT/EP2008/064873
§ 371 (c)(1),
(2), (4) Date: Oct. 22, 2010

(87) PCT Pub. No.: WO2009/059945
PCT Pub. Date: May 14, 2009

(65) Prior Publication Data
US 2011/0060139 A1  Mar. 10, 2011

(30) Foreign Application Priority Data
Nov. 8, 2007  (GB) .................................. 0721935.5

(51) Int. Cl.
| | | |
|---|---|---|
| *A61K 31/7016* | (2006.01) | |
| *C07H 5/06* | (2006.01) | |
| *C07H 15/12* | (2006.01) | |
| *C07H 15/16* | (2006.01) | |
| *C07H 15/203* | (2006.01) | |
| *C08B 37/00* | (2006.01) | |

(52) U.S. Cl.
CPC .................. *C07H 15/12* (2013.01); *C07H 5/06* (2013.01); *C07H 15/203* (2013.01)
USPC .......... 536/29.1; 536/22.1; 536/55; 536/55.1; 536/55.2; 536/55.3; 514/53; 514/61; 514/62

(58) Field of Classification Search
None
See application file for complete search history.

(56) References Cited

U.S. PATENT DOCUMENTS 4,384,998 A * 5/1983 Durette .......................... 540/200

FOREIGN PATENT DOCUMENTS

| AT | 503 400 A1 | 10/2007 |
| EP | 1 577 316 | 9/2005 |
| JP | 2004-352673 | 12/2004 |
| WO | 2004/058789 | 7/2004 |
| WO | WO 2007/033329 | 3/2007 |
| WO | WO 2007/104311 | 9/2007 |

OTHER PUBLICATIONS

Soderman, O. et al "Polyhydroxyl-based surfactants . . ." Curr. Opin. Colloid Inter. Science (2000) vol. 4, pp. 391-401.*
Lichtenthaler, F. et al "Carbohydrates as green raw materials . . ." C. R. Chimie (2004) vol. 7, pp. 65-90.*
Rico-Lattes, I. et al "Synthesis of new sugar-based surfactants . . ." Colloids and Surfaces A: Physiochem. Eng. Aspects (1997) vol. 123-124, pp. 37-48.*
Witzemann, "Products of condensation between glucose and p-phenetidine", Abstract from Atti accad. Lincei, vol. 6, No. 2, 1925, pp. 337-342, 1 page.
Heyns, et al., "Conversion of fructose with amino acids to glucosamino acids", Angewandte Chem., vol. 68, No. 9, 1956, pp. 334-335.
Fischer, "Isoglucosamine", Berichte der Deutschen Chemischen Gesellschaft, vol. 19, 1886, pp. 1920-1924.
Fischer, "Compounds of glucoses and sucroses with phenylhydrazine", Berichte der Deutschen Chemischen Gesellschaft, vol. 17, 1885, pp. 579-584.
Maillard, "Action of Amino Acids on Sugars. Formation of Melanoidins in a Methodical Way", Comptes rendus, vol. 154, 1912, pp. 66-68.

(Continued)

*Primary Examiner* — Leigh Maier
(74) *Attorney, Agent, or Firm* — Pillsbury Winthrop Shaw Pittman LLP

(57) ABSTRACT

A 1,2-dideoxy-1,2-diamino oligosaccharide or polysaccharide in its free base, salt or metal-complex form as shown in General Formula 1 and derivative thereof is described.

General Formula 1.

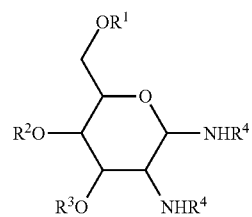

$R^1$, $R^2$ and $R^3$ are each independently selected from the group consisting of H and a carbohydrate moiety, with the proviso that at least one of the groups $R^1$, $R^2$ or $R^3$ is a carbohydrate moiety; $R^4$ is selected from the group consisting of: H, optionally substituted $C_{1-20}$-alkyl, optionally substituted heteroalkyl, optionally substituted $C_{2-20}$-alkenyl, optionally substituted $C_{2-20}$-alkynyl, optionally substituted $C_{3-10}$-cycloalkyl, optionally substituted heterocyclyl, optionally substituted aryl, and optionally substituted heteroaryl.

16 Claims, No Drawings

(56) References Cited

OTHER PUBLICATIONS

Heyns, et al., "Ketosylamine rearrangement in the reaction of D-threo-pentulose (D-xylulose) with amines and amino acids to give 2-alkylamino-2-deoxypentoses", Chem. Ber., vol. 101, No. 8, 1968, pp. 2800-2806.

Heyns, et al., "Formation of an amino sugar from D-fructose and ammonia", Z. Naturforsch, vol. 7b, 1952, pp. 486-488.

Carson, "The Reaction of Fructose with Isopropylamine and Cyclohexylamine", J. Am. Chem. Soc., vol. 77, No. 7, 1955, pp. 1881-1884.

Carson, "The Reaction of Fructose with Aliphatic Amines", J. Am. Chem. Soc., vol. 77, No. 22, 1955, pp. 5957-5960.

Heyns, et al., "The formation and preparation of D-glucosamine from fructose and ammonia", Chem. Ber., vol. 86, 1953, pp. 1453-1462.

Carson, "Reaction of Fructose with Benzylamine", J. Am. Chem. Soc., vol. 78, No. 15, 1956, pp. 3728-3731.

Heyns, et al., "Ketosylamine rearrangement in the reaction of D-threo-pentulose (D-xylulose) with amines and amino acids to give 2-alkylamino-2-deoxypentoses", Chem. Ber., vol. 101, No. 8, 1968, pp. 2807-2814.

Heyns, et al., "Preparation and behavior of 2-(N-amino acid substituted) 2-deoxyglucoses ("glucose-aminoacids") from glycine, alanine, leucine, and fructose", Chem. Ber., vol. 90, 1957, pp. 1374-1386.

Heyns, et al., "The formation of 2-aminoaldoses by rearrangement of ketosylamines", Chem. Ber., vol. 90, 1957, pp. 2039-2049.

Heyns, et al., "Preparation and properties of additional N-substituted 2-amino-2-deoxyaldoses from D-fructose and amino acids", Chem Ber., vol. 91, 1958, pp. 2750-2762.

Heyns, et al., "Reaction of L-tryptophan and L-histidine with hexoses", Chem Ber., vol. 97, No. 2, 1964, pp. 415-418.

Heyns, et al., "Reaction of fructose and sorbose with ammonia and amines", Chem. Ber., vol. 88, 1955, pp. 1551-1555.

Heyns, et al., "Ketosylamine rearrangementof D-threo-pentulose (D-xylulose) with α-amino acids", Chem. Ber., vol. 103, No. 9, 1970, pp. 2873-2876.

Wrodnigg, et al., "The Heyns Rearrangement Revisited: An Exceptionally Simple Two-Step Chemical Synthesis of D-Lactosamine from Lactulose", Angew. Chem. Int. Ed., vol. 38, No. 6, 1999, pp. 827-828.

Stütz, et al., "An Exceptionally Simple Chemical Synthesis of O-Glycosylated D-Glucosamine Derivatives by Heyns Rearrangement of the Corresponding O-Glycosyl Fructoses", Journal of Carbohydrate Chemistry, vol. 22, No. 5, 2003, pp. 253-265.

International Search Report as issued for PCT/EP2008/064873, dated May 29, 2009.

Zanini, et al., "Synthesis of Novel Dendritic Glycosides", Tetrahedron Letters, vol. 36, No. 41, 1995, pp. 7383-7386.

Walker, et al., "The Synthesis of oligosaccharide-l-asparagine Compounds. Part VI. Di-N-acetylisochitobiose-l-asparagine, 2-acetamido-6-O-(2-acetamido-2-deoxy-β-d-glucopyranosyl)-1-N-(1-aspart-4-oyl)-2-deoxy-β-d-glucopyranosylamine", Carbohydrate Research, vol. 32, 1974, pp. 145-154.

Piispanen, et al., "Improved Method for the Synthesis of 2-Alkylamino-2-deoxy-D-glucopyranose and 1,2-Dialkylannino-1,2-dideoxy-D-(N)-β-glucoside", J. Org. Chem., vol. 68, 2003, pp. 628-630.

Japanese Office Action dated Sep. 3, 2013 in corresponding Japanese Patent Application No. 2010-532559.

\* cited by examiner

1,2-DIDEOXY-1,2-DIAMINO OLIGOSACCHARIDES AND POLYSACCHARIDES AND DERIVATIVES THEREOF

CROSS-REFERENCE TO RELATED APPLICATIONS

This is the U.S. National Stage of PCT/EP2008/064873, filed Nov. 3, 2008, which in turn claims priority to Great Britain Patent Application No. 0721935.5, filed Nov. 8, 2007, the entire contents of both applications are incorporated herein by reference in their entireties.

FIELD OF THE INVENTION

The present invention provides novel 1,2-dideoxy-1,2-diamino oligosaccharides and methods suitable for the preparation of the title compounds in their free base, salt or metal-complex forms, and derivatives thereof. The present invention also provides new uses of 1,2-dideoxy-1,2-diamino oligosaccharides including large-scale production of 2-deoxy-2-amino oligosaccharides.

BACKGROUND OF THE INVENTION

One of most commonly applied chemical reactions between an amino acid and a reducing sugar is the Maillard reaction. The reactive carbonyl group of the sugar interacts with the nucleophilic amino group of the amino acid resulting interesting but poorly characterized odor and flavor molecules. This reaction is the basis of the flavoring industry, since the type of amino acid determines the resulting flavor. In this the process, numerous different flavor compounds are created. Although this reaction has been used since ancient times, the reaction is named after the chemist Louis-Camille Maillard who investigated it in the 1910s.[1]

Related reactions are the Amadori rearrangement and the Heyns rearrangement. The Amadori rearrangement[2] is an acid or base catalyzed isomerisation of the N-glycoside of an aldose or the glycosylamine to the corresponding 1-amino-1-deoxy-ketose, while during the Heyns rearrangement ketoses react with amines forming ketosylamines which further isomerise to the corresponding 2-amino-2-deoxy-aldoses. The second rearrangement was first described by Fisher[3] and later further investigated by Heyns and Koch.[4] The Heyns rearrangement reaction was further studied by Carson's and Heyns's labs and numerous different experiments were performed using fructose and other monosaccharides as starting materials.[5]

Up to now the isolated yields of Heyns reactions have been moderate in most cases because this reaction suffers from a variety of problems such as competition between hydrolysis and rearrangement of the initial ketosylamines, epimer formation at position 2, separation problems, side reactions, further degradation entering into the Maillard reaction cascade etc. These difficulties caused the absence of synthetic application of this rearrangement reaction. Recently an improved method was published to increase the yield of the rearranged product from fructose.[6]

Experiments using oligosaccharides as a starting compound for the Heyns reaction are rarely performed and, where they are performed, the process involves the isolation of labile ketosylamine. Stütz's group did valuable work using lactulose and turanose as a starting ketose for the reaction[7] isolating lactosamine and nigerosamine as products.

To date, no oligosaccharides have been described in the literature having a reducing end structure of 1,2-dideoxy-1,2-diamino, although these compounds might be expected to be easily available by Heyns reaction of oligosaccharides characterized by a keto-hexose reducing end structural motif.

WO2007/104311 describes a range of novel compounds having useful functionality. An aim of certain aspects of the present invention is to provide an improved route to such compounds and novel intermediates for use in such a process.

SUMMARY OF THE INVENTION

The present invention provides novel 1,2-dideoxy-1,2-diamino oligosaccharide derivatives and methods for the preparation of these products in their free base, salt or metal-complex forms avoiding the isolation of labile ketosyl amines.

Furthermore, the present invention provides novel methods for the transformation of the titled 1,2-dideoxy-1,2-diamino oligosaccharides into oligosaccharides containing 2-deoxy-2-amino hexose residues at their reducing end.

The first aspect of the present invention provides 1,2-dideoxy-1,2-diamino oligosaccharides or polysaccharides in their free base, salt or metal-complexed forms.

The first embodiment of the first aspect of the present invention provides novel 1→4 linked 1,2-dideoxy-1,2-diamino disaccharide derivatives in their free base, salt or metal-complexed forms.

The second embodiment of the first aspect of the present invention provides novel 1→6 linked 1,2-dideoxy-1,2-diamino disaccharide derivatives in their free base, salt or metal-complexed forms.

The third embodiment of the first aspect of the present invention provides novel 1→3 linked 1,2-dideoxy-1,2-diamino disaccharide derivatives in their free base, salt or metal-complexed forms.

The second aspect of the present invention provides novel methods suitable for the preparation of 1,2-dideoxy-1,2-diamino oligosaccharides or polysaccharides and the isolation of such compounds in their free base, salt or metal-complexed forms.

The first embodiment of the second aspect of the present invention provides novel methods suitable for the preparation of 1→4 linked 1,2-dideoxy-1,2-diamino disaccharides and the isolation of such compounds in their free base, salt or metal-complexed forms.

The second embodiment of the second aspect of the present invention provides novel methods suitable for the preparation of 1→6 linked 1,2-dideoxy-1,2-diamino disaccharides and the isolation of such compounds in their free base, salt or metal-complexed forms.

The third embodiment of the second aspect of the present invention provides novel methods suitable for the preparation of 1→3 linked 1,2-dideoxy-1,2-diamino disaccharides and the isolation of such compounds in their free base, salt or metal-complexed forms.

The third aspect of the present invention provides methods for the preparation of 2-deoxy-2-amino oligosaccharides from 1,2-dideoxy-1,2-diamino oligosaccharides.

The first embodiment of the third aspect of the present invention provides methods for the preparation of 1→4 linked 2-deoxy-2-amino oligosaccharides from 1→4 linked 1,2-dideoxy-1,2-diamino oligosaccharides in which the indicated 1→4 linkage is maintained between the reducing end sugar residue and at least one of the connected sugar residues.

The second embodiment of the third aspect of the present invention provides methods for the preparation of 1→6 linked 2-deoxy-2-amino oligosaccharides from 1→6 linked 1,2-dideoxy-1,2-diamino oligosaccharides in which the indicated 1→6 linkage is maintained between the reducing end sugar residue and at least one of the connected sugar residues.

The third embodiment of the third aspect of the present invention provides methods for the preparation of 1→3 linked 2-deoxy-2-amino oligosaccharides from 1→3 linked 1,2-dideoxy-1,2-diamino oligosaccharides in which the indicated 1→3 linkage is maintained between the reducing end sugar residue and at least one of the connected sugar residues.

Further, the present invention provides for the use of 1,2-dideoxy-1,2-diamino oligosaccharides or polysaccharides in the preparation of other oligosaccharide or polysaccharide products. Such a use may be by means of conversion of 1,2-dideoxy-1,2-diamino oligosaccharides or polysaccharides to 2-amino-2-deoxy oligosaccharides or polysaccharides, and in particular a conversion of 1,2-dideoxy-1,2-diamino disaccharides to 2-amino-2-deoxy disaccharides, such as lactosamine. Further, such a use may be by means of conversion of 1,2-dideoxy-1,2-diamino oligosaccharides or polysaccharides to N-substituted 2-amino-2-deoxy oligosaccharides or polysaccharide, and in particular a conversion of 1,2-dideoxy-1,2-diamino disaccharides to N-substituted 2-amino-2-deoxy disaccharides, such as N-alkyllactosamines.

It is further envisaged in the present invention that the 1,2-dideoxy-1,2-diamino oligosaccharides or polysaccharides may find application as medicaments, as pharmaceuticals, as diagnostic agents, in diagnostic kits, as a detergent or surfactant, or as a food additive or component of food products.

DETAILED DESCRIPTION OF THE INVENTION

Glucosamine containing oligosaccharides and their derivatives play important roles in biological systems. This simple monosaccharide residue can be found in many biologically active oligosaccharides such as blood group antigens, cell surface antigens and human milk oligosaccharides. There is a significant demand for large scale and economical production of glucosamine containing oligosaccharides such as lactosamine, N-acetyllactosamine and numerous other oligosaccharide structures. Most methods suitable for the production of such compounds use complex glycosylation strategies building the oligosaccharides—including even disaccharides—from smaller building blocks via conjugation chemistries. These methods are extremely expensive and require highly skilled workforce. In contrast, the present invention provides a new avenue for the preparation of such important carbohydrates via simple chemical transformation of readily available oligosaccharides. Such methods can be performed via the formation of novel 1,2-dideoxy-1,2-diamino oligosaccharides. Thus, the present invention represents a breakthrough for accessing such important oligosaccharide derivatives in cheap and economical ways.

The present invention facilitates the formation of any oligosaccharide carrying a 2-amino-2-deoxy-glycopyranose residue at its reducing end. The general procedure requires a base or enzyme catalyzed aldose-ketose isomerization followed by the formation of novel 1,2-dideoxy-1,2-diamino disaccharides and higher oligo/polysaccharides. Further, the present invention provides novel methods to transform the novel 1,2-dideoxy-1,2-diamino disaccharides and higher oligo/polysaccharides into 1,2-dideoxy-1,2-diamino oligosaccharides/polysaccharides.

The main subject of the present invention is to provide novel 1,2-dideoxy-1,2-diamino oligosaccharides, novel methods for the preparation of the titled compounds and the transformation of those into 2-deoxy-2-amino oligosaccharides.

The first aspect of the present invention provides novel 1,2-dideoxy-1,2-diamino disaccharides and higher oligo/polysaccharides either in their free base, salt (mono or divalent salts) or metal-complex forms characterized by General Formula 1.

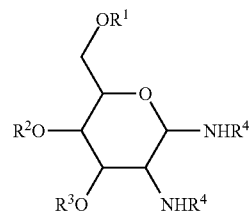

General Formula 1.

wherein $R^1$, $R^2$ and $R^3$ are each independently selected from the group consisting of H and carbohydrate moiety, with the proviso that at least one carbohydrate moiety is always selected;

$R^4$ is selected from the group consisting of: optionally substituted $C_{1-20}$-alkyl, optionally substituted heteroalkyl, optionally substituted $C_{2-20}$-alkenyl, optionally substituted $C_{2-20}$-alkynyl, optionally substituted $C_{3-10}$-cycloalkyl, optionally substituted heterocyclyl, optionally substituted aryl, and optionally substituted heteroaryl. In particular $R^4$ is selected from the group consisting of optionally substituted $C_{1-6}$-alkyl, optionally substituted heteroalkyl, optionally substituted heterocyclyl, optionally substituted aryl, and optionally substituted heteroaryl. More preferably, $R^4$ is selected from the group consisting of optionally substituted benzyl, optionally substituted benzhydryl, optionally substituted trityl, and optionally substituted naphthylmethyl.

Definition: When used herein, the expression "carbohydrate moiety" is intended to encompass (but is not limited to) derivatised and underivatised mono- and oligo-saccharides, iminosugars, thiosugars, C-glycosides, and carbocycles. The carbohydrate structural motif is directly- and/or indirectly linked via covalent linkages including but not limited to ether, acyl or glycosidic bonds to the heteroatom of which the carbohydrate structural motif is said to be a substitutent.

In the present context, the term "alkyl" is intended to mean a linear or branched hydrocarbon group having 1 to 20 carbon atoms, such as methyl, ethyl, propyl, iso-propyl, butyl, tert-butyl, iso-butyl, pentyl, hexyl, octyl, nonyl, decyl, undecyl, dodecyl, etc.

For the purposes of this specification, the term "optionally substituted" means that the group in question may either carry a substituent or may be unsubstituted.

More generally, in connection with the term "alkyl" the term "optionally substituted" is intended to mean that the group in question may be substituted one or several times, preferably 1-3 times, with group(s) selected from the group consisting of: hydroxyl (which when bound to an unsaturated carbon atom may be present in the tautomeric keto form), $C_{1-6}$-alkoxy (i.e. $C_{1-6}$-alkyl-oxy), $C_{2-6}$-alkenyloxy, carboxy, oxo (forming a keto or aldehyde functionality), $C_{1-6}$-alkoxycarbonyl, $C_{1-6}$-alkylcarbonyl, formyl, aryl, aryloxycarbonyl, aryloxy, arylamino, arylcarbonyl, heteroaryl, heteroarylamino, heteroaryloxycarbonyl, heteroaryloxy, heteroarylcarbonyl, amino, mono- and di($C_{1-6}$-alkyl)amino, carbamoyl, mono- and di($C_{1-6}$-alkyl)aminocarbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkylcarbonylamino, cyano, guanidino, carbamido, $C_{1-6}$-alkyl-sulphonyl-amino, aryl-sulphonyl-amino, heteroaryl-sulphonyl-amino, $C_{1-6}$-alkanoyloxy, $C_{1-6}$-alkyl-sulphonyl, $C_{1-6}$-alkyl-sulphinyl, $C_{1-6}$-alkylsulphonyloxy, nitro, $C_{1-6}$-alkylthio, and halogen; where any aryl and heteroaryl may be substituted as specifically described below for "optionally substituted aryl and heteroaryl", and any alkyl, alkoxy, and the like representing substituents may be substituted with hydroxy, $C_{1-6}$-alkoxy, $C_{2-6}$-alkenyloxy, amino, mono- and di($C_{1-6}$-alkyl)amino, carboxy, $C_{1-6}$-alkyl-carbonylamino, halogen, $C_{1-6}$-alkylthio, $C_{1-6}$-alkyl-sulphonyl-amino, or guanidino.

Preferably, the substituents are selected from the group consisting of: hydroxy (which when bound to an unsaturated carbon atom may be present in the tautomeric keto form), $C_{1-6}$-alkoxy (i.e. $C_{1-6}$-alkyl-oxy), $C_{2-6}$-alkenyloxy, carboxy, oxo (forming a keto or aldehyde functionality), $C_{1-6}$-alkyl-carbonyl, formyl, aryl, aryloxy, arylamino, arylcarbonyl, heteroaryl, heteroarylamino, heteroaryloxy, heteroarylcarbonyl, amino, mono- and di($C_{1-6}$-alkyl)amino; carbamoyl, mono- and di($C_{1-6}$-alkyl)aminocarbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkylcarbonylamino, guanidino, carbamido, $C_{1-6}$-alkyl-sulphonyl-amino, $C_{1-6}$-alkyl-sulphonyl, $C_{1-6}$-alkyl-sulphinyl, $C_{1-6}$-alkylthio, and halogen; where any aryl and heteroaryl may be substituted as specifically described below for "optionally substituted aryl and heteroaryl".

Definition: The term "oligosaccharide" includes natural or unnatural carbohydrates in which natural or unnatural monosaccharides—independently of whether they are pyranoses or furanoses, or aldoses or ketoses—are linked into homo- or hetero oligomers/polymers characterized by either linear or branched structures via glycosidic linkages. Preferably, the size of homo- or hetero oligomers covers all disaccharides, trisaccharides, tetrasaccharides, pentasaccharides, etc up to the incorporation of 16 sugar residues.

Definition: The term "polysaccharide" includes natural or unnatural carbohydrates in which more than 16 natural or unnatural monosaccharides—independently of whether they are pyranoses or furanoses, or aldoses or ketoses—are linked into homo- or hetero oligomers/polymers characterized by either linear or branched structures via glycosidic linkages.

The term "salt" is intended to include acid addition salts. Illustrative examples of acid addition salts are pharmaceutically acceptable salts formed with organic or inorganic acids. Examples of such organic salts are those with maleic, fumaric, benzoic, ascorbic, succinic, oxalic, bis-methylene-salicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, benzenesulfonic, and theophylline acetic acids, as well as the 8-halotheophyllines, for example 8-bromotheophylline. Examples of such inorganic salts are those with hydrochloric, hydrobromic, sulfuric, sulfamic, phosphoric, and nitric acids. Thus, the term "an acid addition salt thereof" used herein is intended to comprise such salts.

Furthermore, in cases where the compound carries more than one basic group such as an amino group within a molecule, monoprotonation results in monovalent and diprotonation creates divalent salts with the corresponding anions.

Furthermore, the compounds as well as any intermediates or starting materials may also be present in hydrate form.

Moreover, it should be understood that the compounds may be present as racemic mixtures or the individual stereoisomers such as enantiomers or diastereomers. The present invention encompasses each and every of such possible stereoisomers (e.g. enantiomers and diastereomers) as well as racemates and mixtures enriched with respect to one of the possible stereoisomers.

Definition: The term "complex" means that organic compounds that are the subject of the present invention may be coordinatively linked to any metal ions carrying one, two three or more positive charges alone or along with other organic or inorganic ligands. Such complexes may link to carbohydrate residues via any of their anomeric forms, including cases when one carbohydrate molecule creates multiple coordinative linkages including but not limited to 1,2-cis or 1,2-trans adducts.

The first embodiment of the first aspect of the present invention provides novel 1→4 linked 1,2-dideoxy-1,2-diamino disaccharide derivatives either in their free base, salt (mono or divalent salts) or metal-complex forms characterized by General Formula 2.

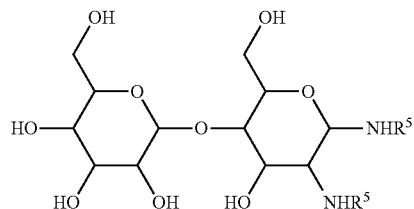

General Formula 2.

wherein $R^5$ is selected from the group consisting of: optionally substituted benzyl, optionally substituted benzhydryl, optionally substituted trityl, optionally substituted naphthylmethyl or optionally substituted allyl groups The second embodiment of the first aspect of the present invention provides novel 1→6 linked 1,2-dideoxy-1,2-diamino disaccharide derivatives either in their free base, salt (mono or divalent salts) or metal-complex forms characterized by General Formula 3.

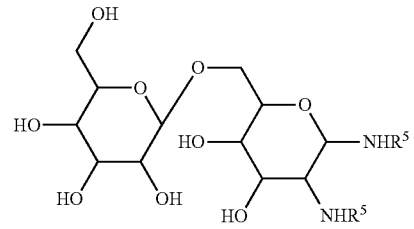

General Formula 3.

wherein $R^5$ is as defined at General Formula 2.

The third embodiment of the first aspect of the present invention provides novel 1→3 linked 1,2-dideoxy-1,2-diamino disaccharide derivatives either in their free base, salt (mono or divalent salts) or metal-complex form characterized by General Formula 4.

General Formula 4.

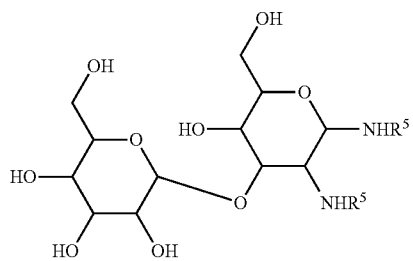

wherein $R^5$ is defined as in General Formula 2.

The second aspect of the present invention provides novel methods suitable for the preparation of 1,2-dideoxy-1,2-diamino oligosaccharides/polysaccharides as shown in General Reaction Scheme 1. Oligosaccharides having a ketose unit at the reducing end can serve as starting materials for Heyns rearrangements using any primary amine as a reagent. Amines with bulky substituents may be used to prevent the formation of the axial isomers during the reaction if the introduction of an equatorial alkylamino function is desired. Similarly, amines with less bulky substituents are used to prevent the formation of the equatorial isomers during the reaction if the introduction of an axial alkylamino function is desired. According to the inventors' best knowledge, these 1,2-dideoxy-1,2-diamino oligosaccharides/polysaccharides have never previously been prepared, isolated and fully characterized. The present invention represents the very first case in which these oligosaccharides are prepared, isolated, characterized and used for further elaboration in their pure forms.

General Reaction Scheme 1

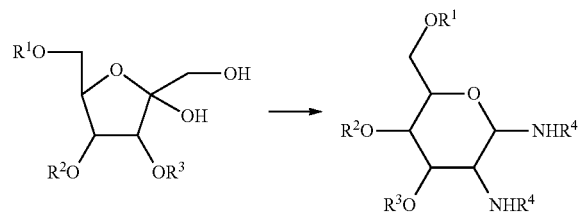

wherein $R^1$, $R^2$, $R^3$ and $R^4$ are as defined in General Formula 1

Typically the Heyns reaction is carried out in solution or using the amine-reagent also as the solvent for the reaction in the presence or absence of acid or an oxide, including protic and/or Lewis acids and/or metaloxide and/or oxides of non-metallic atoms. Amine reagents can include any organic molecules having at least one primary amine function. Solvents including but not limited to methanol, 1,4-dioxane, DMF (dimethylformamide), THF (tetrahydrofuran), etc and mixtures thereof can be used for such a chemical transformation. The temperature of the reaction may be between 10-80° C., preferably between 30-50° C. The acid or oxide used for the reaction may be any inorganic or organic protic acid such as HCl, HBr, $H_2SO_4$, p-toluol sulphonic acid, acetic acid, formic acid etc; any Lewis acid such as $AlCl_3$, $ZnCl_2$, $CuBr_2$ etc; any polymer bound acids such as strong or weak ion exchange resins; any acidic or neutral insoluble catalysts such as Zeolites; any oxides such as $P_2O_5$, $S_2O_3$, $SO_2$, $Al_2O_3$ etc. The reaction time typically varies from 2 hours to 7 days depending on the structure of the substrate, the set temperature and the nature of the amine reagent and the acid or oxide used. The products are typically obtained in yields of 20 to 95%.

The first embodiment of the second aspect of the present invention provides novel methods suitable for the preparation of 1→4 linked 1,2-dideoxy-1,2-diamino disaccharides and their isolation in their free base, salt or metal-complex form, as shown in General Reaction Scheme 2.

General Reaction Scheme 2

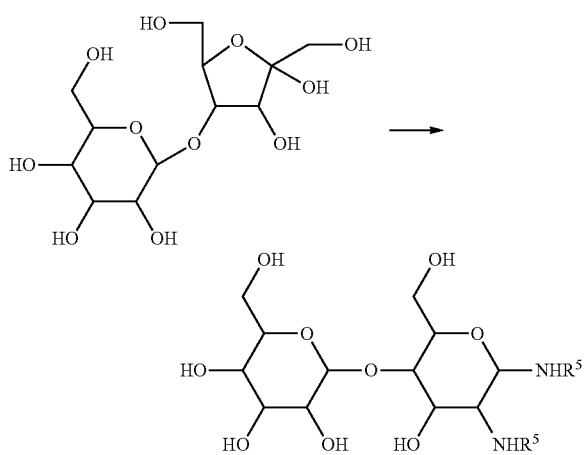

wherein $R^5$ is as defined in General Formula 2

It is an important feature of the present invention that any 1→4 linked disaccharides having a ketose residue at their reducing end can be transformed into 1→4 linked 1,2-dideoxy-1,2-diamino disaccharides having a 2-amino-2-deoxy glycopyranose unit at the reducing end. Any 1→4 linked disaccharides carrying a ketose unit at the reducing can be used as a starting material for the reaction. Optionally, a base catalyzed aldose-ketose isomerization reaction can be performed using known methods prior to the amine treatment if the precursor carries an aldose structural feature at the reducing end. Preferably maltulose or lactulose are used for the reaction. However, it is emphasized that any disaccharide may be used, even one having an aldose carbohydrate unit at the reducing end, as this could be transformed into a keto-disaccharide via base treatment as well known by a person skilled in the art. It is also emphasized that any kind of primary amine can be used as a reagent. Preferably, however, aliphatic amines, especially optionally substituted -benzylamine, -benzhydryl-amine, -tritylamine, -naphthylmethylamine or -allylamine and derivatives thereof suitable for Heyns rearrangement are used.

Typically, the reaction is carried out either in solution or in the amine-reagent itself (using the reagent as a solvent) in the presence or absence of acids and/or oxides. Solvents including but not limited to methanol, 1,4-dioxane, DMF, tetrahydrofuran, etc and mixtures thereof can be used for such a chemical transformation. Preferably, the amine reagent—if that is a liquid—is used as a solvent for the reaction. Suitable amines may be optionally substituted benzylamine, -benzhydrylamine, -tritylamine, -naphthylmethylamine or -allylamine. The temperature of the reaction may be between 10-80° C., preferably between 30-50° C. The acid or oxide used for the reaction can be an inorganic or organic protic acid such as HCl, HBr, $H_2SO_4$, p-toluol sulphonic acid, acetic acid, formic acid etc, a Lewis acid such as $AlCl_3$, $ZnCl_2$, $CuBr_2$ etc; a polymer bound acid such as ion exchange resins; insoluble acidic or neutral catalysts such as Zeolites; or an oxide such as $P_2O_5$, $S_2O_3$, $SO_2$, $Al_2O_3$ etc. The reaction time typically varies from 2 hours to 7 days depending on the structure of the substrate, the set temperature and the nature of the amine reagent and the acid used. A crude reaction mixture can be obtained after the removal of the excess amine reagent and/or solvent used for the reaction. The removal of these materials can be performed by using distillation under reduced pressure or by extractive work-up procedures. The products are obtained in their free base, salt (mono or divalent salt) or in metal-complex form by selective precipitation or crystallization. Acids used to create the salt form of the products may be any inorganic or organic protic acid such as HCl, HBr, $H_2SO_4$, p-toluol sulphonic acid, acetic acid, formic acid etc, and the process is usually carried out under anhydrous conditions to avoid the hydrolysis of the functional group at the anomeric position. The metal ions used to create the complexes include but are not limited to Cu(II), Cu(I), Zn (II), Co(II), Pt(I), Pd(I), Fe(II), Fe(III), AMU), etc and any other metal known in art to create such complexes. The products are typically obtained in yields of 20 to 95%.

The second embodiment of the second aspect of the present invention provides novel methods suitable for the preparation of 1→6 linked 1,2-dideoxy-1,2-diamino disaccharides and the isolation of these compounds in their free base, salt or metal-complex forms, as shown in General Reaction Scheme 3.

General Reaction Scheme 3

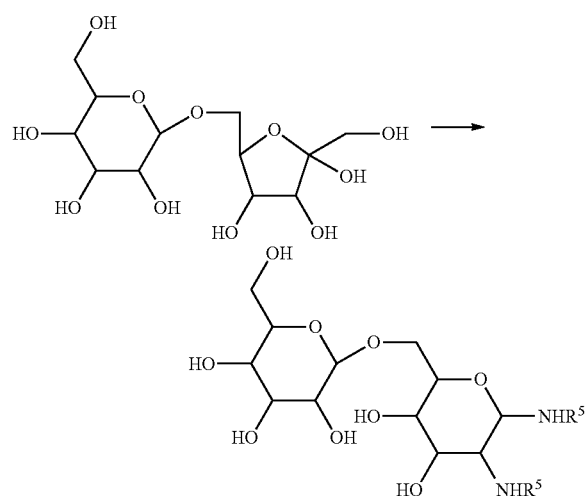

wherein $R^5$ is as defined in General Formula 2

Thus, any 1→6 linked disaccharides having a ketose residue at their reducing end can be transformed into 1→6 linked 1,2-dideoxy-1,2-diamino disaccharides having a 2-amino-2-deoxy-glycopyranose structural feature at the reducing end. Any 1→6 linked disaccharides carrying a ketose motif at the reducing end can be used as a starting material for the reaction. Optionally, a base catalyzed aldose-ketose isomerization reaction can be performed using known methods prior to the amine treatment if the precursor carries an aldose structural feature at the reducing end. Preferably, palatinose (αGlc1→6Fru) is used for the reaction. Any kind of primary amine can be used as a reagent. Preferably, aliphatic amines, and most preferably benzylamine, benzhydrylamine, tritylamine, naphthylmethylamine or allylamine and derivatives of these amines are used for the invention.

The reactions are carried out as described in the first embodiment of the second aspect of the present invention, and the products are isolated in similar yields.

The third embodiment of the second aspect of the present invention provides novel methods suitable for the preparation of 1→3 linked 1,2-dideoxy-1,2-diamino disaccharides and the isolation of these compounds in their free base, salt or metal-complex forms as shown in General Reaction Scheme 4.

General Reaction Scheme 4

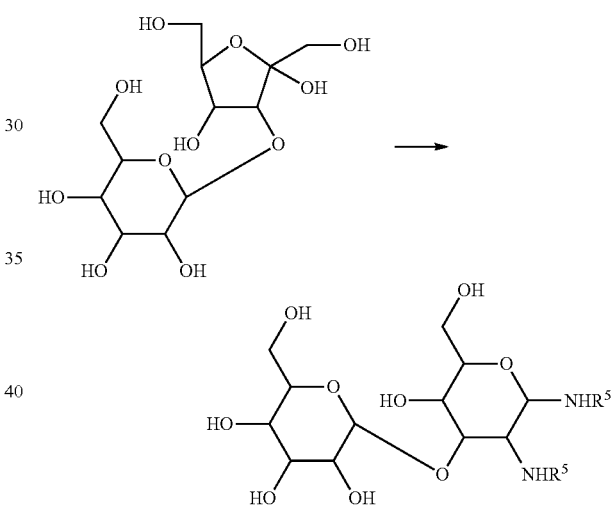

wherein $R^5$ is as defined in General Formula 2

Any 1→3 linked disaccharides carrying a ketose structural feature at the reducing end can be used as a starting material. Optionally a base catalyzed aldose-ketose isomerization reaction can be performed using known methods prior to the amine treatment if the precursor carries an aldose structural feature at the reducing end. Preferably turanose (αGlc1→3Fru) is used for the reaction. Any kind of primary amine can be used as a reagent. Preferably aliphatic amines, and most preferably benzylamine, benzhydrylamine, tritylamine, naphthylmethylamine or allylamine and derivatives thereof are used.

The reactions are carried out as described in the first embodiment of the second aspect of the present invention, and the products are isolated in similar yields.

The third aspect of the present invention provides novel methods suitable for the preparation of 2-deoxy-2-amino oligosaccharides from 1,2-dideoxy-1,2-diamino oligosaccharides as shown in General Reaction Scheme 5.

General Reaction Scheme 5.

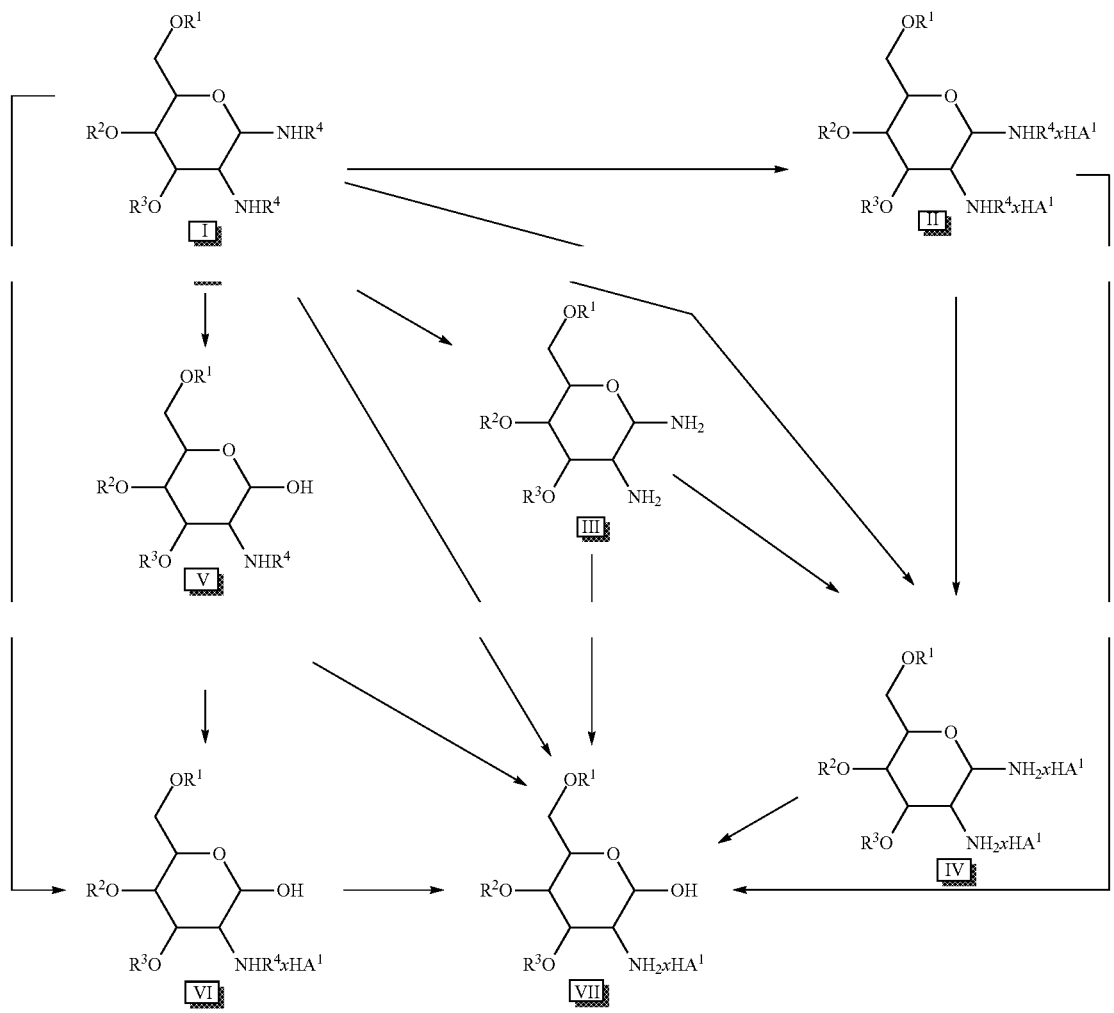

wherein $R^1$, $R^2$, $R^3$, and $R^4$ are as defined in General Formula 1

$A^1$ is any inorganic or organic anion known in the art. The anion can be mono- or multivalent, and may form a complex salt. Examples of suitable anions are halides, anions of organic acids, anions of inorganic acids, etc. Specific examples thereof are chloride (a), bromide ($Br^-$), iodide ($I^-$), acetate, lactate, maleate, fumarate, oxalate, salicylate, sulphate, hydrogensulphate, phosphate, hydrogenposphate, dihydrogenphosphate, nitrate, etc.

Oligosaccharides that contain a ketose structural motif at the reducing end play important roles in biological processes. The preparation of these compounds has usually been performed by glycosylation of the optionally protected glucosamine derivatives. The present invention provides novel methods to transfer the previously described novel 1,2-dideoxy-1,2-diamino oligosaccharides (Compound I) into 2-deoxy-2-amino oligosaccharides (Compound VII) without any glycosylation step.

A preferred method for the preparation of 2-deoxy-2-amino oligosaccharides involves the formation of a salt of the 1,2-dideoxy-1,2-diamino oligosaccharides (Compound I→Compound II). The formation of these compounds (Compound II) is performed under inert atmosphere in anhydrous conditions to avoid the hydrolytic cleavage of the functional group at the anomeric position. Acids used to create the salt form are any inorganic or organic protic acid such as HCl, HBr, $H_2SO_4$, p-toluol sulphonic acid, acetic acid, formic acid etc. The solvents used for the salt formation include but are not limited to methanol, ethanol, acetone, THF, etc. 2-Deoxy-2-amino oligosaccharides (Compound VII) can be obtained after the removal of $R^4$ residues and the hydrolysis of the anomeric amine into a hydroxyl function in one step. Solvents for this reaction include but are not limited to methanol, ethanol, water, acetic acid, ethyl acetate, etc and mixtures thereof. The catalyst used for the removal of the $R^4$ substituents include but are not limited to palladium, platinum, rhodium or nickel in any form such as palladium on carbon, platinum oxide, or Raney nickel. Pressure can be applied for the reaction of between 1 and 50 bar. If the removal of the protecting group is performed under anhydrous conditions the intermediate can be isolated (Compound IV) which then can be hydrolyzed further to give the title 2-deoxy-2-amino oligosaccharides (Compound VII).

A more preferred method for the preparation of 2-deoxy-2-amino oligosaccharides involves a metal catalyzed reaction of a substance of General Formula 1 in the absence of acid, resulting in the isolation of intermediates (Compound III) wherein the $R^4$ substituents are removed and primary amines are in position 1 and 2 of the reducing end of the oligosaccharides in their free base form. Solvents used for the removal of $R^4$ substituents include but are not limited to methanol, ethanol, water, acetic acid, ethyl acetate, etc and the mixtures of thereof. The metal used for the reaction includes but is not limited to palladium, platinum, rhodium or nickel in any form such as palladium on carbon, platinum oxide, or Raney nickel. Pressure can be applied for the reaction of between 1 and 50 bar. The isolated intermediates (Compound III) can be subsequently transformed into their salt form under anhydrous conditions (Compound IV), and hydrolyzed finally into the target compounds (Compound VII). Acids used to create the salt form are any inorganic or organic protic acid such as HCl, HBr, $H_2SO_4$, p-toluol sulphonic acid, acetic acid, formic acid etc, and the process is usually carried out under anhydrous conditions to avoid hydrolysis in the anomeric position. The solvents used for the salt formation include but are not limited to methanol, ethanol, acetone, THF, etc. Optionally, if the same reaction is performed in the presence of water, Compound III can be directly hydrolyzed into Compound VII.

Another preferred method for the preparation of 2-deoxy-2-amino oligosaccharides involves a metal catalyzed reaction of a substance of General Formula 1 in the presence of acid, isolating an intermediate (Compound IV) wherein the $R^4$ substituents are removed and primary amines are in position 1 and 2 of the reducing sugar residue in their salt form. Solvents used for the removal of $R^4$ substituents include but are not limited to methanol, ethanol, water, acetic acid, ethyl acetate, etc and mixtures thereof. The metal used for the reaction includes but is not limited to palladium, platinum, rhodium or nickel in any form such as palladium on carbon, platinum oxide, or Raney nickel. Pressure can be applied for the reaction of between 1 and 50 bar. Acids used for the reaction may be any inorganic or organic protic acid such as HCl, HBr, $H_2SO_4$, p-toluol sulphonic acid, acetic acid, formic acid etc. The process is usually carried out under anhydrous conditions to avoid the hydrolysis of the functional group at the anomeric position. The final 2-deoxy-2-amino oligosaccharides (Compound VII) are obtained after hydrolysis of the aldosamine.

A further preferred method for the preparation of 2-deoxy-2-amino oligosaccharides involves the hydrolytic cleavage of the anomeric amine of compound of I in the absence of acid, obtaining compound V. Solvents used for the reaction include but are not limited to methanol, ethanol, water, ethyl acetate, etc and mixtures thereof. The isolated intermediate (compound V) can be directly transformed to Compound VII with a metal catalyzed reaction in the presence of acid. Solvents used for the removal of $R^4$ substituents in position 2 of the reducing sugar include but are not limited to methanol, ethanol, THF, water, acetic acid, ethyl acetate, etc and mixtures thereof. The metal used for the reaction includes but is not limited to palladium, platinum, rhodium or nickel in any form such as palladium on carbon, platinum oxide, or Raney nickel. Pressure can be applied for the reaction of between 1 and 50 bar. Acids used for the reaction may be any inorganic or organic protic acid such as HCl, HBr, $H_2SO_4$, p-toluol sulphonic acid, acetic acid, formic acid etc. Another two step transformation of compound V into compound VII is possible wherein the salt of the amine in position 2 of the reducing sugar is isolated first as an intermediate (Compound VI). Acids used to create the salt form may be any inorganic or organic protic acid such as HCl, HBr, $H_2SO_4$, p-toluol sulphonic acid, acetic acid, formic acid etc. The solvents used for the salt formation include but are not limited to water, methanol, ethanol, acetone, THF, etc. 2-Deoxy-2-amino oligosaccharides (Compound VII) can be obtained after metal catalyzed reaction of compound VI wherein the $R^4$ substituent is removed from position 2 of the reducing oligosaccharide. Solvents used for the removal of $R^4$ substituent include but are not limited to methanol, ethanol, water, acetic acid, ethyl acetate, etc and mixtures thereof. The metal used for the reaction includes but is not limited to palladium, platinum, rhodium or nickel in any form such as palladium on carbon, platinum oxide, or Raney nickel. Pressure can be applied for the reaction of between 1 and 50 bar.

A more preferred method for the preparation of 2-deoxy-2-amino oligosaccharides involves the hydrolytic cleavage of the anomeric amine of I in the presence of acid, obtaining compound VI. Solvents used for the reaction include but are not limited to methanol, ethanol, water, acetone, THF, ethyl acetate, etc and mixtures thereof. Acids used for the reaction may be any inorganic or organic protic acid such as HCl, HBr, $H_2SO_4$, p-toluol sulphonic acid, acetic acid, formic acid etc. The isolated compound VI can be further transferred into 2-deoxy-2-amino oligosaccharides with a metal catalyzed reaction as described above.

The most preferred method for the preparation of 2-deoxy-2-amino oligosaccharides involves the metal catalyzed reaction of Compound I to remove the $R^4$ substituents in the presence of acid and water, wherein hydrolysis at the anomeric position also occurs (Compound I→compound VII). The metal used for the reaction includes but is not limited to palladium, platinum, rhodium or nickel in any form such palladium on carbon, platinum oxide, or Raney nickel. Pressure can be applied for the reaction of between 1 and 50 bar. Acids used for the reaction may be any inorganic or organic protic acid such as HCl, HBr, $H_2SO_4$, p-toluol sulphonic acid, acetic acid, formic acid etc. The solvents used for the salt formation include but are not limited to water, methanol, ethanol, acetone, THF, etc.

The first embodiment of the third aspect of the present invention provides methods for the preparation of 1→4 linked 2-deoxy-2-amino oligosaccharides from 1→4 linked 1,2-dideoxy-1,2-diamino oligosaccharides as shown in General Reaction Scheme 6.

General Reaction Scheme 6.

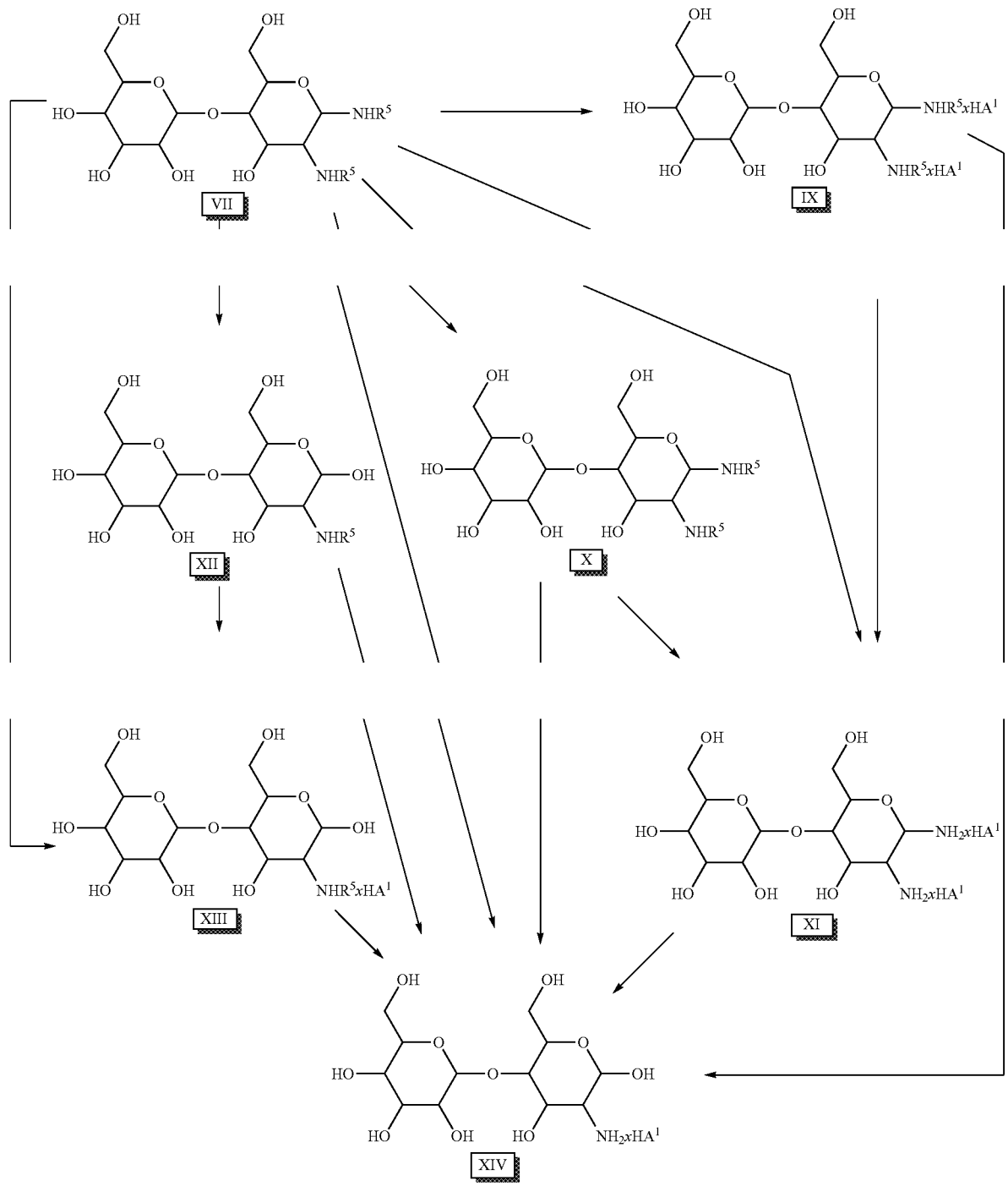

wherein $R^5$ is as defined in General Formula 2.

$A^1$ is as defined in General Reaction Scheme 5.

The reactions can be carried out following the methods described in the third aspect of the present invention providing intermediates of (Compounds IX, X, XI, XII and XIII) and the product (Compound XIV) in similar isolated yields.

The second embodiment of the third aspect of the present invention provides methods for the preparation of 1→6 linked 2-deoxy-2-amino oligosaccharides from 1→6 linked 1,2-dideoxy-1,2-diamino oligosaccharides as shown in General Reaction Scheme 7.

General Reaction Scheme 7.

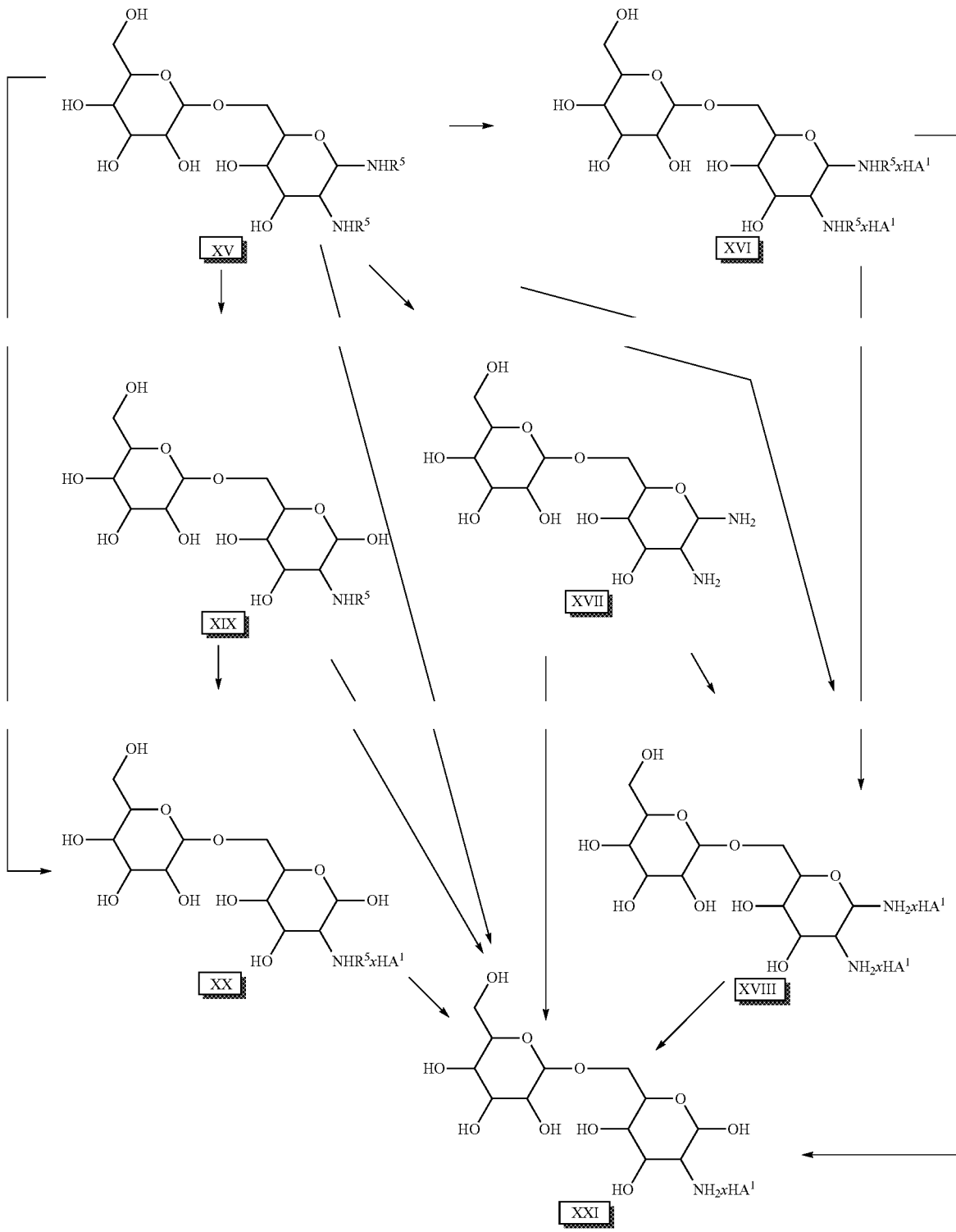

wherein $R^5$ is as defined in General Formula 2.

$A^1$ is as defined in General Reaction Scheme 5.

All reactions are carried out as described in the third aspect of the present invention via intermediates of (Compounds XVI, XVII, XVIII, XIX and XX) providing the product of (Compound XXI) in similar yields.

The third embodiment of the third aspect of the present invention provides methods for the preparation of 1→3 linked 2-deoxy-2-amino oligosaccharides from 1→3 linked 1,2-dideoxy-1,2-diamino oligosaccharides as shown in General Reaction Scheme 8.

General Reaction Scheme 8.

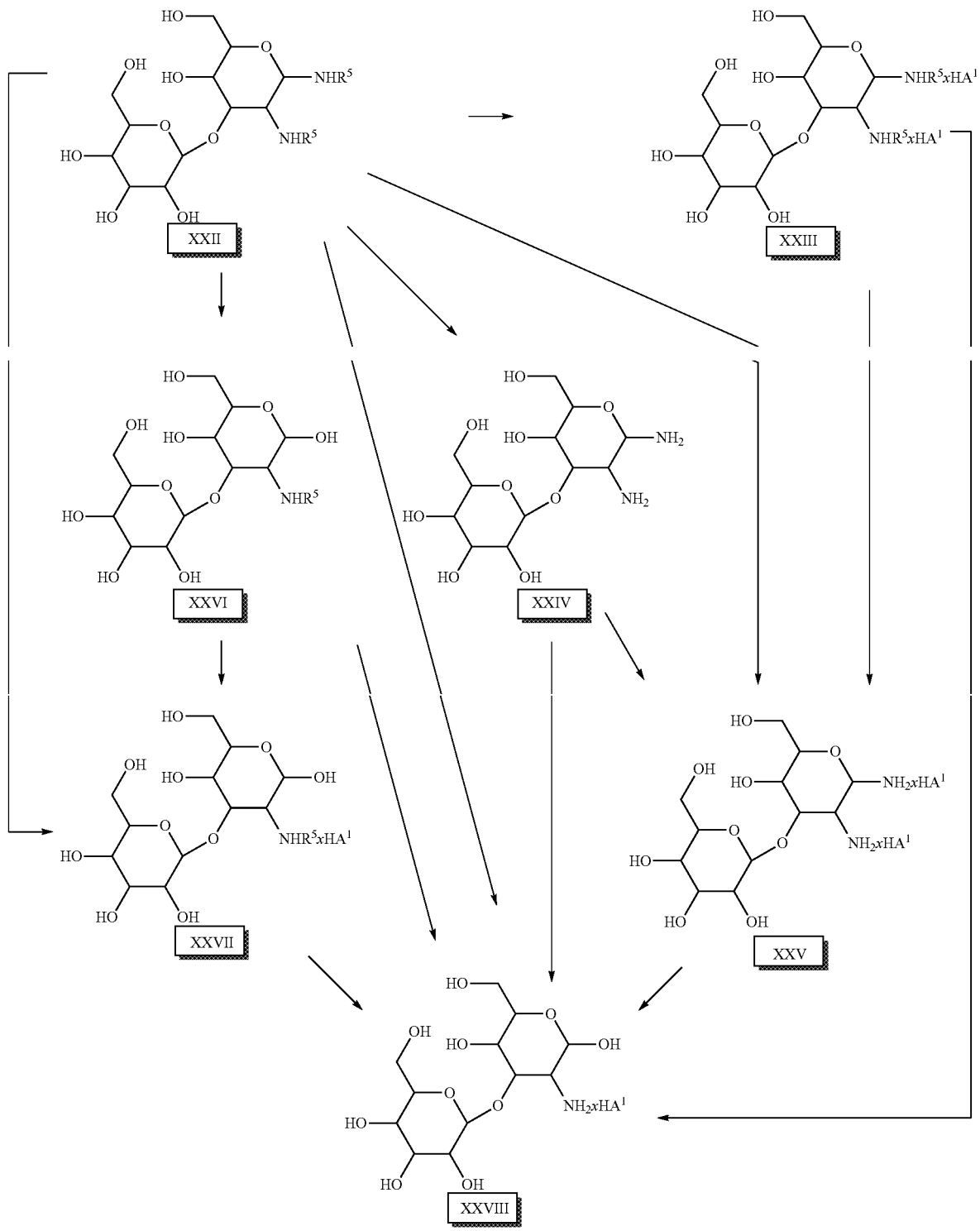

wherein $R^5$ is as defined in General Formula 2.

$A^1$ is as defined in General Reaction Scheme 5.

All reactions are carried out as described in the third aspect of the present invention including all intermediates (Compounds XXIII, XXIV, XXV, XXVI and XXVII) providing the product (Compound XXVIII) in similar yields.

Experimental Section

General Methods

General methods for the preparation of 1,2-dideoxy-1,2-diamino oligosaccharides in which precursors characterized by General Formula 1-4 are transformed into Compounds I, VIII, XV and XXII.

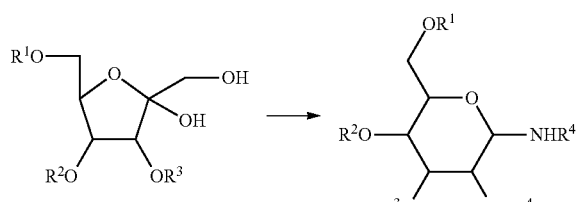

Typically the reaction is carried out in solution or in the amine-reagent itself using the reagent also as a solvent, in the presence or absence of an acid or/and oxide. Solvents including but not limited to methanol, 1,4-dioxane, DMF, tetrahydrofuran, etc and mixtures thereof can be used for such a chemical transformation. Preferably the amine reagent, if that is a liquid, is used as a solvent for the reaction. Suitable amines include optionally substituted benzylamine, -benzhydrylamine, -tritylamine, -naphthylmethylamine or -allylamine. The temperature of the reaction can be in the range 10-80° C. Preferably, temperatures in the range 30-50° C. are selected, and more preferably 40-45° C. The acid or oxide used for the reaction can be any inorganic or organic protic acid such as HCl, HBr, $H_2SO_4$, p-toluol sulphonic acid, acetic acid, formic acid etc; any Lewis acid such as $AlCl_3$, $ZnCl_2$, $CuBr_2$ etc; any polymer bound acids such as ion exchange resins; acidic or neutral insoluble catalysts such as Zeolites; any oxides such as $P_2O_5$, $S_2O_3$, $SO_2$, $Al_2O_3$ etc. The reaction time typically varies from 2 hours to 7 days depending on the structure of the substrate, the set temperature and the nature of the amine reagent agent and the acid or oxide used. A crude reaction mixture can be obtained after the removal of the excess amine reagent and/or the solvent used for the reaction. The removal of these materials is performed using distillation under reduced pressure or by extractive work-up procedures. The products are obtained in their free base, salt (mono or divalent salt) or in their metal-complex form by selective precipitation or crystallization. Acids used to create the salt form of the products may be any inorganic or organic protic acid such as HCl, HBr, $H_2SO_4$, p-toluol sulphonic acid, acetic acid, formic acid etc, and the process is usually carried out under anhydrous conditions to avoid the hydrolysis of the functional group at the anomeric position. The metals used to create the complex are Cu(II), Cu(I), Zn (II), Co(II), Pt(I), Pd(I), Fe(II) and any other metal known in art to create such complexes. The products are typically obtained in yields of 20 to 95%. General methods for the transformation of compound I→II; compound VIII→IX, compound XV→XVI and compound XXII→XXIII.

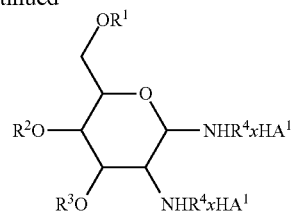

The reactions were carried out under an inert atmosphere to avoid the hydrolytic cleavage of the anomeric position. The crude reaction mixtures obtained from the Heyns reaction were dissolved in organic solvent or solvent mixture, and anhydrous acid added to form the salt which precipitated or crystallized from the mixture. Acids used to create the salts may be any inorganic or organic protic acid such as HCl, HBr, $H_2SO_4$, p-toluol sulphonic acid, acetic acid, formic acid etc. The solvents used for the salt formation may be methanol, ethanol, isopropanol, acetone, THF, etc.

General methods for the transformation of compound I→III; compound VIII→X, compound XV→XVII and compound XXII→XXIV.

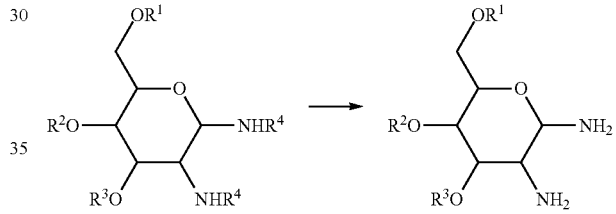

The reactions were performed under inert atmosphere to avoid hydrolysis. The solvent used for the reaction may be methanol, ethanol, isopropanol, ethyl acetate, etc or mixtures thereof. Generally, metal catalyzed hydrogenolysis was used for the removal of $R^4$ substituents. The metal used for the reaction may be palladium, platinum, rhodium or nickel in any form such as palladium on carbon, platinum oxide, or Raney nickel. As the hydrogen source $H_2$-gas, ammoniumformate, formic acid etc, may be used. The pressure applied for the reaction may be selected in the range of from 1 to 50 bar.

General methods for the transformation of compound I→IV; compound VIII→XI, compound XV→XVIII and compound XXII→XXV.

-continued

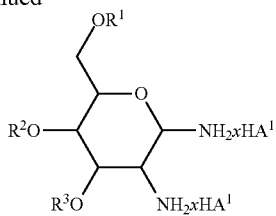

The reactions were performed under inert atmosphere to avoid hydrolysis. The solvent used for the reaction may be methanol, ethanol, acetic acid, ethyl acetate, etc or mixtures thereof. Generally, metal catalyzed hydrogenolysis was used for the removal of $R^4$ substituents. The metal used for the reaction may be palladium, platinum, rhodium or nickel in any form such as palladium on carbon, platinum oxide, or Raney nickel. As the hydrogen source $H_2$-gas, ammonium-formate, formic acid etc, may be used. The pressure applied for the reaction may be selected in the range of from 1 to 50 bar. Acids used to create the salts may be any inorganic or organic protic acid such as HCl, HBr, $H_2SO_4$, p-toluol sulphonic acid, acetic acid, formic acid etc.

General methods for the transformation of compound I→V; compound VIII→XII, compound XV→XIX and compound XXII→XXVI.

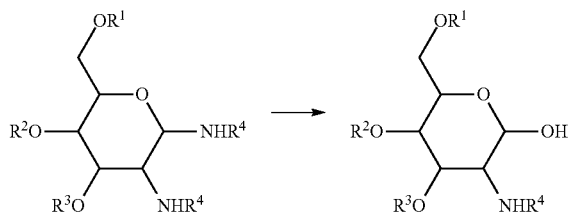

The reactions were performed in solution. Solvents used for the reaction may be water, methanol, ethanol, acetone, isopropanol, ethyl acetate, etc or mixtures thereof with the proviso that water is always selected in at least equimolar amounts to the carbohydrate moiety. The presence of any acid was avoided, but base can be used to facilitate the reaction. Bases used for the reaction may be any inorganic or organic base such as TEA (triethylamine), pyridine, $NaHCO_3$, etc.

General methods for the transformation of compound I→VI; compound VIII→XIII, compound XV→XX and compound XXII→XXVII.

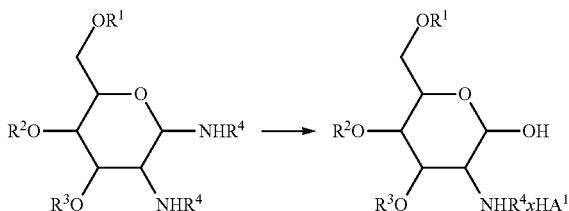

The reactions were performed in solution. Solvents used for the reaction may be water, methanol, ethanol, acetone, isopropanol, ethyl acetate, etc or mixtures thereof with the proviso that water is always selected in at least equimolar amounts to the carbohydrate moiety. Acids used to create the salts and facilitate the reaction may be any inorganic or organic protic acid such as HCl, HBr, $H_2SO_4$, p-toluol sulphonic acid, acetic acid, formic acid etc.

General methods for the transformation of compound I→VII; compound VIII→XIV, compound XV→XXI and compound XXII→XXVIII.

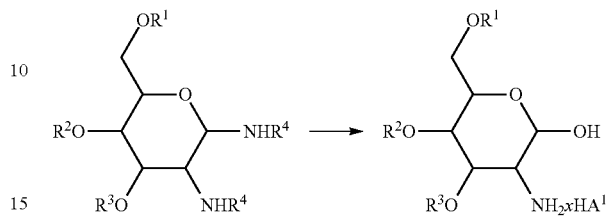

The reactions were carried out in solution. Solvents used for the reaction may be methanol, ethanol, water, isopropanol, acetic acid, ethyl acetate, etc or mixtures thereof with the proviso that water is always selected in at least equimolar amounts to the carbohydrate moiety. Generally, metal catalyzed hydrogenolysis was used for the removal of $R^4$ substituent. The metal used for the reaction may be palladium, platinum, rhodium or nickel in any form such as palladium on carbon, platinum oxide, or Raney nickel. As the hydrogen source $H_2$-gas, ammonium-formate, formic acid etc, may be used. The pressure applied for the reaction may be selected in the range of from 1 to 50 bar. Acids used to create the salts may be any inorganic or organic protic acid such as HCl, HBr, $H_2SO_4$, p-toluol sulphonic acid, acetic acid, formic acid etc.

General methods for the transformation of compound II→IV; compound IX→XI, compound XVI→XVIII and compound XXIII→XXV.

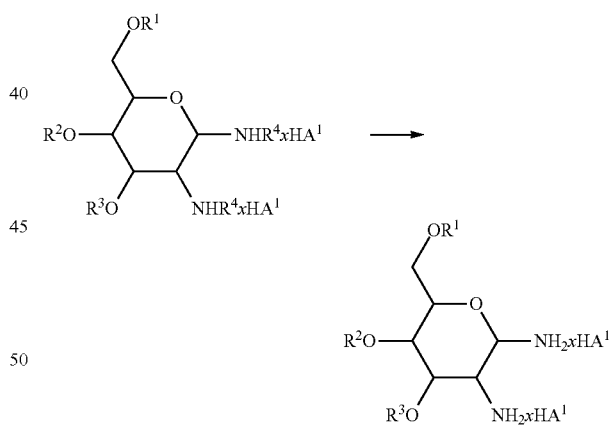

The reactions were performed under inert atmosphere to avoid hydrolysis. Solvents used for the reaction may be methanol, ethanol, acetic acid, ethyl acetate, etc or mixtures thereof. Generally, metal catalyzed hydrogenolysis was used for the removal of $R^4$ substituents. The metal used for the reaction may be palladium, platinum, rhodium or nickel in any form such as palladium on carbon, platinum oxide, or Raney nickel. As the hydrogen source $H_2$-gas, ammonium-formate, formic acid etc, may be used. The pressure applied for the reaction may be selected in the range of from 1 to 50 bar. Acids that can be used to facilitate the reaction may be any inorganic or organic protic acid such as HCl, HBr, $H_2SO_4$, p-toluol sulphonic acid, acetic acid, formic acid etc.

General methods for the transformation of compound II→VII; compound IX→XIV, compound XVI→XXI and compound XXIII→XXVIII.

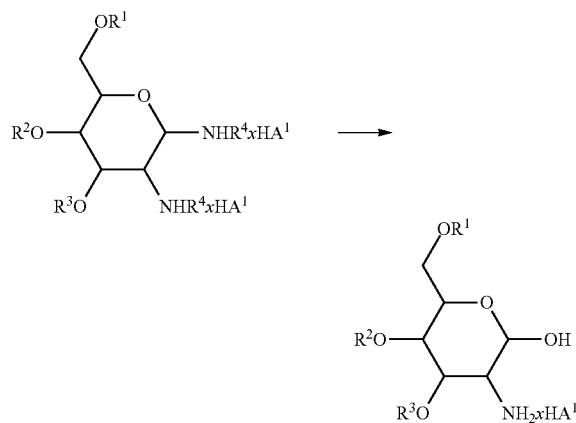

The reactions were carried out in solution. Solvents used for the reaction may be methanol, ethanol, water, isopropanol, acetic acid, ethyl acetate, etc or mixtures thereof with the proviso that water is always selected in at least equimolar amounts to the carbohydrate moiety. Generally, metal catalyzed hydrogenolysis was used for the removal of $R^4$ substituent. The metal used for the reaction may be palladium, platinum, rhodium or nickel in any form such as palladium on carbon, platinum oxide, or Raney nickel. As the hydrogen source $H_2$-gas, ammonium-formate, formic acid etc, may be used. The pressure applied for the reaction may be selected in the range of from 1 to 50 bar. Acids that can be used to facilitate the reactions may be any inorganic or organic protic acid such as HCl, HBr, $H_2SO_4$, p-toluol sulphonic acid, acetic acid, formic acid etc.

General methods for the transformation of compound III→IV; compound X→XI, compound XVII→XVIII and compound XXIV→XXV.

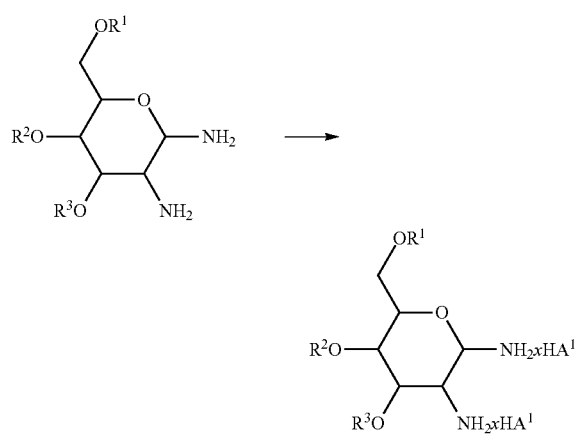

The reactions were carried out under inert atmosphere to avoid the hydrolytic cleavage of the anomeric position. The crude diamino derivatives were dissolved in organic solvent or solvent mixture, and anhydrous acid was added to form the salt which precipitated or crystallized from the mixture. Acids used to create the salts may be any inorganic or organic protic acid such as HCl, HBr, $H_2SO_4$, orthophosphoric acid, p-toluol sulphonic acid, acetic acid, formic acid etc. The solvents used for the salt formation may be methanol, ethanol, isopropanol, acetone, THF, etc.

General methods for the transformation of compound III→VII; compound X→XIV, compound XVII→XXI and compound XXIV→XXVIII.

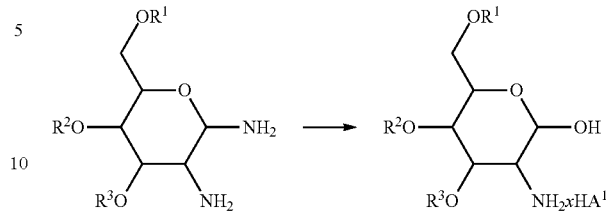

The reactions were performed in solution. Solvents used for the reaction may be water, methanol, ethanol, acetone, isopropanol, ethyl acetate, etc or mixtures thereof with the proviso that water is always selected in at least equimolar amounts to the carbohydrate moiety. Acids used to create the salts and facilitate the reaction may be any inorganic or organic protic acid such as HCl, HBr, $H_2SO_4$, p-toluol sulphonic acid, acetic acid, formic acid etc.

General methods for the transformation of compound IV→VII; compound XI→XIV, compound XVIII→XXI and compound XXV→XXVIII.

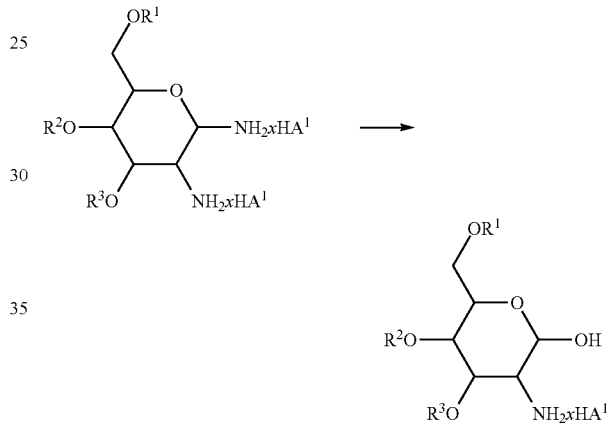

The reactions were performed in solution. Solvents used for the reaction may be water, methanol, ethanol, acetone, isopropanol, ethyl acetate, etc or mixtures thereof with the proviso that water is always selected in at least equimolar amounts to the carbohydrate moiety. Acids that can be used to facilitate the reaction may be any inorganic or organic protic acid such as HCl, HBr, $H_2SO_4$, p-toluol sulphonic acid, acetic acid, formic acid etc.

General methods for the transformation of compound V→VI; compound XII→XIII, compound XIX→XX and compound XXVI→XXVII.

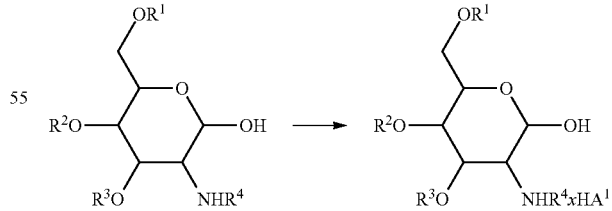

The reactions were performed in solution. Solvents used for the reaction may be water, methanol, ethanol, acetone, isopropanol, ethyl acetate, etc or mixtures thereof with the proviso that water is always selected in at least equimolar amounts to the carbohydrate moiety. Acids used for the reaction may be any inorganic or organic protic acid such as HCl, HBr, $H_2SO_4$, p-toluol sulphonic acid, acetic acid, formic acid etc.

General methods for the transformation of compound V→VII; compound XII→XIV, compound XIX→XXI and compound XXVI→XXVIII.

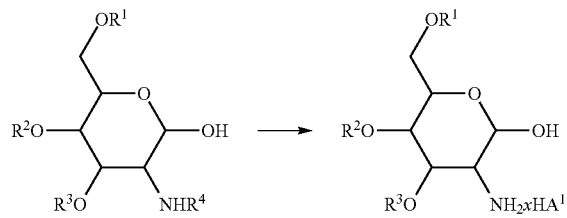

The reactions were carried out in solution. Solvents used for the reaction may be methanol, ethanol, water, isopropanol, acetic acid, ethyl acetate, etc or mixtures thereof. Generally, metal catalyzed hydrogenolysis was used for the removal of the $R^4$ substituent. The metal used for the reaction may be palladium, platinum, rhodium or nickel in any form such as palladium on carbon, platinum oxide, or Raney nickel. As the hydrogen source $H_2$-gas, ammonium-formate, formic acid etc, may be used. The pressure applied for the reaction may be selected in the range 1 to 50 bar. Acids used to facilitate the hydrogenolysis and create the salt may be any inorganic or organic protic acid such as HCl, HBr, $H_2SO_4$, p-toluol sulphonic acid, acetic acid, formic acid etc.

General methods for the transformation of compound VI→VII; compound XIII→XIV, compound XX→XXI and compound XXVII→XXVIII.

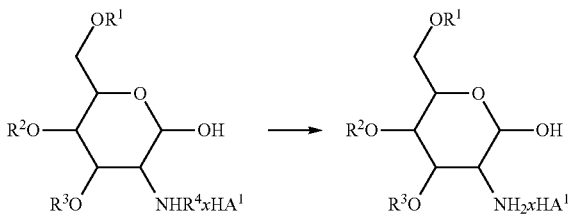

The reactions were carried out in solution. Solvents used for the reaction may be methanol, ethanol, water, isopropanol, acetic acid, ethyl acetate, etc or mixtures thereof. Generally, metal catalyzed hydrogenolysis was used for the removal of $R^4$ substituent. The metal used for the reaction may be palladium, platinum, rhodium or nickel in any form such as palladium on carbon, platinum oxide, or Raney nickel. As the hydrogen source $H_2$-gas, ammonium-formate, formic acid etc, may be used. The pressure applied for the reaction may be selected in the range 1 to 50 bar. Acids that can be used to facilitate the hydrogenolysis may be any inorganic or organic protic acid such as HCl, HBr, $H_2SO_4$, p-toluol sulphonic acid, acetic acid, formic acid etc.

EXAMPLES

1. Preparation of 1,2-dideoxy-1,2-dibenzylamino lactose

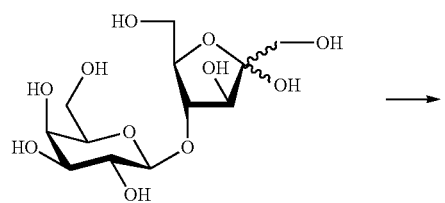

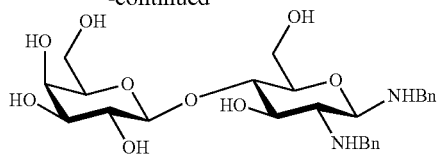

$1^{st}$ experiment: Lactulose (50 g) and benzylamine hydrochloride (1 g) were added to benzylamine (100 mL) at 0° C. and the white suspension stirred at 0° C. for 4 days. Then acetone (300 mL) was added to the mixture followed by the addition of hexane (300 mL). The mixture was shaken then the upper phase discarded. To the lower phase again acetone (300 mL) and hexane (300 mL) were added and extracted. The phases were separated and the extraction repeated once with the same amounts of solvents. Finally, the lower phase was concentrated obtaining the crude reaction mixture. The product was crystallized after addition of methanol (100 mL). The white crystals were filtered, washed and dried. Yield: 20 g beta isomer. The mother liquor contains a mixture of alpha and beta anomers.

$2^{nd}$ experiment: Lactulose (50 g) and zinc chloride (100 mg) were added to benzylamine (100 mL) at 0° C. and the white suspension stirred at 40° C. for 3 days. Then acetone (300 mL) was added to the mixture followed by the addition of hexane (300 mL). The mixture was shaken then the upper phase discarded. To the lower phase again acetone (300 mL) and hexane (300 mL) were added and extracted. The phases were separated and the extraction repeated once with the same amounts of solvents. Finally, the lower phase was concentrated obtaining the crude reaction mixture. The product was crystallized after addition of methanol (100 mL). The white crystals were filtered, washed and dried. Yield: 18 g beta isomer.

$3^{rd}$ experiment: Lactulose (50 g) and trifluoroacetic acid (100 μL) were added to benzylamine (100 mL) at 0° C. and the white suspension stirred at 40° C. for 4 days. Then acetone (300 mL) was added to the mixture followed by the addition of hexane (300 mL). The mixture was shaken then the upper phase discarded. To the lower phase again acetone (300 mL) and hexane (300 mL) were added and extracted. The phases were separated and the extraction repeated once with the same amounts of solvents. Finally, the lower phase was concentrated obtaining the crude reaction mixture. The product was crystallized after addition of methanol (100 mL). The white crystals were filtered, washed and dried. Yield: 21 g beta isomer.

$4^{th}$ experiment: Lactulose (50 g) and $AlCl_3$ (100 mg) were added to benzylamine (100 mL) at 0° C. and the white suspension stirred at 40° C. for 4 days. Then acetone (300 mL) was added to the mixture followed by the addition of hexane (300 mL). The mixture was shaken then the upper phase discarded. To the lower phase again acetone (300 mL) and hexane (300 mL) were added and extracted. The phases were separated and the extraction repeated once with the same amounts of solvents. Finally, the lower phase was concentrated obtaining the crude reaction mixture. The product was crystallized after addition of methanol (100 mL). The white crystals were filtered, washed and dried. Yield: 17 g beta isomer.

$5^{th}$ experiment: Lactulose (50 g) and $P_2O_5$ (100 mg) were added to benzylamine (100 mL) at 0° C. and the white suspension stirred at 40° C. for 4 days. Then acetone (300 mL) was added to the mixture followed by the addition of hexane (300 mL). The mixture was shaken then the upper phase discarded. To the lower phase again acetone (300 mL) and hexane (300 mL) were added and extracted. The phases are separated and the extraction repeated once with the same amounts of solvents. Finally, the lower phase was concentrated obtaining the crude reaction mixture. The product was crystallized after addition of methanol (100 mL). The white crystals were filtered, washed and dried. Yield: 20 g beta isomer.

6$^{th}$ experiment: Lactulose (50 g) and $P_2O_5$ (100 mg) were added to benzylamine (100 mL) at 0° C. and the white suspension stirred at 40° C. for 4 days. Then acetone (100 mL) was added to the mixture followed by the addition of hexane (200 mL). The mixture was shaken then the upper phase discarded. To the lower phase again acetone (100 mL) and hexane (200 mL) were added and extracted. The phases were separated and the extraction repeated once with the same amounts of solvents. Finally, the lower phase was concentrated obtaining the crude reaction mixture. The product was crystallized after addition of methanol (100 mL). The white crystals were filtered, washed and dried. Yield: 22 g beta isomer.

7$^{th}$ experiment: Lactulose (50 g) and $P_2O_5$ (100 mg) were added to benzylamine (100 mL) at 0° C. and the white suspension stirred at 40° C. for 4 days. Then solvents were removed with high vacuum obtaining the crude reaction mixture. The product was crystallized after addition of methanol (100 mL). The white crystals were filtered, washed and dried. Yield: 13 g beta isomer.

8$^{th}$ experiment: Lactulose (50 g) and $P_2O_5$ (100 mg) were added to benzylamine (100 mL) at 0° C. and the white suspension stirred at 40° C. for 4 days. Then acetone (300 mL) was added to the mixture followed by the addition of hexane (300 mL). The mixture was shaken then the upper phase discarded. To the lower phase again acetone (300 mL) and hexane (300 mL) were added and extracted. The phases were separated and the extraction repeated once with the same amounts of solvents. Finally, the lower phase was concentrated obtaining the crude reaction mixture. The product was crystallized after addition of methanol (50 mL). The white crystals were filtered, washed and dried. Yield: 16 g beta isomer.

9$^{th}$ experiment: Lactulose (50 g) and $P_2O_5$ (100 mg) were added to benzylamine (100 mL) at 0° C. and the white suspension stirred at 40° C. for 4 days. Then acetone (300 mL) was added to the mixture followed by the addition of hexane (300 mL). The mixture was shaken then the upper phase discarded. To the lower phase again acetone (300 mL) and hexane (300 mL) were added and extracted. The phases were separated and the extraction repeated once with the same amounts of solvents. Finally, the lower phase was concentrated obtaining the crude reaction mixture. The product was crystallized after addition of methanol (500 mL). The white crystals were filtered, washed and dried. Yield: 16.5 g beta isomer.

10$^{th}$ experiment: Lactulose (50 g) and benzylamine hydrochloride (1 g) were added to benzylamine (100 mL) at 0° C. and the white suspension stirred at 80° C. for 1 day. Then acetone (100 mL) was added to the mixture followed by the addition of hexane (200 mL). The mixture was shaken then the upper phase discarded. To the lower phase again acetone (100 mL) and hexane (200 mL) were added and extracted. The phases were separated and the extraction repeated once with the same amounts of solvents. Finally, the lower phase was concentrated obtaining the crude reaction mixture. The product was crystallized after addition of methanol (100 mL). The white crystals were filtered, washed and dried. Yield: 8 g beta isomer. The mother liquor contains a mixture of alpha and beta anomers.

11$^{th}$ experiment: Lactulose (50 g) and benzylamine hydrochloride (1 g) were added to benzylamine (100 mL) at 0° C. and the white suspension stirred at 40° C. for 4 day. Then acetone (100 mL) was added to the mixture followed by the addition of hexane (200 mL). The mixture was shaken then the upper phase discarded. To the lower phase again acetone (100 mL) and hexane (200 mL) were added and extracted. The phases were separated and the extraction repeated once with the same amounts of solvents. Finally, the lower phase was concentrated obtaining the crude reaction mixture. The product was precipitated after addition of ether (1 L). The yellow precipitate was filtered, washed and dried. Yield: 55 g yellow powder.

12$^{th}$ experiment: Lactulose (50 g) and benzylamine hydrochloride (1 g) were added to benzylamine (100 mL) at 0° C. and the white suspension stirred at 50° C. for 65 h. Then acetone (300 mL) was added to the mixture followed by the addition of hexane (300 mL). The mixture was shaken then the upper phase discarded. To the lower phase again acetone (300 mL) and hexane (300 mL) were added and extracted. The phases were separated and the extraction repeated once with the same amounts of solvents. Finally, the lower phase was concentrated obtaining the crude reaction mixture. The product was crystallized after addition of acetone (200 mL). The yellow crystals were filtered, washed and dried. Yield: 30 g beta isomer.

13$^{th}$ experiment: Lactulose (50 g) and benzylamine hydrochloride (1 g) were added to benzylamine (100 mL) at 0° C. and the white suspension stirred at 0° C. for 4 days. Then acetone (300 mL) was added to the mixture followed by the addition of hexane (300 mL). The mixture was shaken then the upper phase discarded. To the lower phase again acetone (300 mL) and hexane (300 mL) were added and extracted. The phases were separated and the extraction repeated once with the same amounts of solvents. Finally, the lower phase was concentrated obtaining the crude reaction mixture. The product was crystallized after addition of methanol (100 mL) and MTBE (methyl tert-butyl ether) (100 mL). The yellow crystals were filtered, washed and dried. Yield: 20.5 g.

14$^{th}$ experiment: Lactulose (50 g) and $AlCl_3$ (100 mg) were added to benzylamine (50 mL) at 0° C. and the white suspension stirred at 45° C. for 4 days. Then acetone (100 mL) was added to the mixture followed by the addition of hexane (200 mL). The mixture was shaken then the upper phase discarded. To the lower phase again acetone (100 mL) and hexane (200 mL) were added and extracted. The phases were separated and the extraction repeated once with the same amounts of solvents. Finally, the lower phase was concentrated obtaining the crude reaction mixture. The product was crystallized after addition of methanol (80 mL). The white crystals were filtered, washed and dried. Yield: 19 g beta isomer.

15$^{th}$ experiment: Lactulose (75% quality) (50 g) and benzylamine hydrochloride (1 g) were added to benzylamine (100 mL) at 0° C. and the white suspension stirred at 0° C. for 4 days. Then acetone (100 mL) was added to the mixture followed by the addition of hexane (200 mL). The mixture was shaken then the upper phase discarded. To the lower phase again acetone (100 mL) and hexane (200 mL) were added and extracted. The phases were separated and the extraction repeated once with the same amounts of solvents. Finally, the lower phase was concentrated obtaining the crude reaction mixture. The product was crystallized after addition of methanol (100 mL). The white crystals were filtered, washed and dried. Yield: 12 g beta isomer.

16$^{th}$ experiment: Lactulose (75% quality) (50 g) and zinc chloride (100 mg) were added to benzylamine (100 mL) at 0° C. and the white suspension stirred at 45° C. for 3 days. Then acetone (100 mL) was added to the mixture followed by the addition of hexane (200 mL). The mixture was shaken then the upper phase discarded. To the lower phase again acetone (100 mL) and hexane (200 mL) were added and extracted. The phases are separated and the extraction repeated once with the same amounts of solvents. Finally, the lower phase was concentrated obtaining the crude reaction mixture. The product was crystallized after addition of methanol (100 mL). The white crystals were filtered, washed and dried. Yield: 11 g beta isomer.

17th experiment: Lactulose (75% quality) (50 g) and AlCl$_3$ (100 mg) were added to benzylamine (100 mL) at 0° C. and the white suspension stirred at 45° C. for 4 days. Then acetone (100 mL) was added to the mixture followed by the addition of hexane (200 mL). The mixture was shaken then the upper phase discarded. To the lower phase again acetone (100 mL) and hexane (200 mL) were added and extracted. The phases were separated and the extraction repeated once with the same amounts of solvents. Finally, the lower phase was concentrated obtaining the crude reaction mixture. The product was crystallized after addition of methanol (100 mL). The white crystals were filtered, washed and dried. Yield: 11 g beta isomer.

18th experiment: Lactulose (75% quality) (50 g) and P$_2$O$_5$ (100 mg) were added to benzylamine (100 mL) at 0° C. and the white suspension stirred at 40° C. for 4 days. Then acetone (100 mL) was added to the mixture followed by the addition of hexane (200 mL). The mixture was shaken then the upper phase discarded. To the lower phase again acetone (100 mL) and hexane (200 mL) were added and extracted. The phases were separated and the extraction repeated once with the same amounts of solvents. Finally, the lower phase was concentrated obtaining the crude reaction mixture. The product was crystallized after addition of methanol (100 mL). The white crystals were filtered, washed and dried. Yield: 12 g beta isomer.

19th experiment: Lactulose (50 g) and Amberlite IR 120 (H$^+$ form) (200 mg) were added to benzylamine (100 mL) at 0° C. and the white suspension stirred at 45° C. for 4 days. Then acetone (100 mL) was added to the mixture followed by the addition of hexane (200 mL). The mixture was shaken then the upper phase discarded. To the lower phase again acetone (100 mL) and hexane (200 mL) were added and extracted. The phases were separated and the extraction repeated once with the same amounts of solvents. Finally, the lower phase was concentrated obtaining the crude reaction mixture. The product was crystallized after addition of methanol (80 mL). The white crystals were filtered, washed and dried. Yield: 23 g beta isomer.

20th experiment: Lactulose (50 g) and zinc chloride (20 g) were added to benzylamine (100 mL) at 0° C. and the white suspension stirred at 40° C. for 3 days. Then acetone (300 mL) was added to the mixture followed by the addition of hexane (300 mL). The mixture was shaken then the upper phase discarded. To the lower phase again acetone (300 mL) and hexane (300 mL) were added and extracted. The phases were separated and the extraction repeated once with the same amounts of solvents. Finally, the lower phase was concentrated obtaining the crude reaction mixture. The Zn complex of the product was isolated after addition of acetone (1 L). The white powder was filtered, washed and dried. Yield: 25 g beta isomer.

21st experiment: Lactulose (50 g) and copper bromide (18 g) were added to benzylamine (100 mL) at 0° C. and the white suspension stirred at 40° C. for 3 days. Then acetone (100 mL) was added to the mixture followed by the addition of hexane (200 mL). The mixture was shaken then the upper phase discarded. To the lower phase again acetone (100 mL) and hexane (200 mL) were added and extracted. The phases were separated and the extraction repeated once with the same amounts of solvents. Finally, the lower phase was concentrated obtaining the crude reaction mixture. The Cu complex of the product was isolated after addition of acetone (1 L). The blue powder was filtered, washed and dried. Yield: 25 g beta isomer.

22nd experiment: Lactulose (50 g) and benzylamine hydrochloride (1 g) were added to benzylamine (75 mL) at 0° C. and the white suspension stirred at 0° C. for 4 days. Then acetone (100 mL) was added to the mixture followed by the addition of hexane (200 mL). The mixture was shaken then the upper phase discarded. To the lower phase again acetone (100 mL) and hexane (200 mL) were added and extracted. The phases were separated and the extraction repeated once with the same amounts of solvents. Finally, the lower phase was concentrated obtaining the crude reaction mixture. The product was crystallized after addition of acetone (100 mL) and HCl gas as a hydrochloride salt. The white crystals were filtered, washed and dried. Yield: 26 g.

23rd experiment: Lactulose (50 g) and P$_2$O$_5$ (100 mg) were added to benzylamine (100 mL) at 0° C. and the white suspension stirred at 40° C. for 4 days. Then acetone (100 mL) was added to the mixture followed by the addition of hexane (200 mL). The mixture was shaken then the upper phase discarded. To the lower phase again acetone (100 mL) and hexane (200 mL) were added and extracted. The phases were separated and the extraction repeated once with the same amounts of solvents. Finally, the lower phase was concentrated obtaining the crude reaction mixture. The product was crystallized after addition of acetone (200 mL) and a calculated amount of orthophosphoric acid as a phosphate salt. The white crystals were filtered, washed and dried. Yield: 23 g.

24th experiment: Lactulose (50 g) and Al$_2$O$_3$ (500 mg) were added to benzylamine (100 mL) at 0° C. and the white suspension stirred at 50° C. for 3 days. Then acetone (300 mL) was added to the mixture followed by the addition of hexane (300 mL). The mixture was shaken then the upper phase discarded. To the lower phase again acetone (300 mL) and hexane (300 mL) were added and extracted. The phases were separated and the extraction repeated once with the same amounts of solvents. Finally, the lower phase was concentrated obtaining the crude reaction mixture. The product was crystallized after addition of methanol (250 mL). The white crystals were filtered, washed and dried. Yield: 25 g beta isomer.

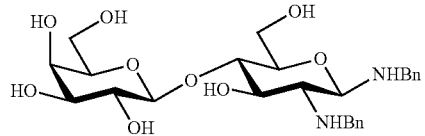

1H NMR. (DMSO d6) δ: 7.34 and 7.18 (2 m, 10H, aromatic), 5.13 (d, 1H, $J_{3',OH}$ 3.93 Hz, 3'-OH), 4.77 (d, 1H, $J_{2',OH}$ 4.77 Hz, 2'-OH), 4.71 (bs, 1H, 3-OH), 4.65 (d, 1H, $J_{6',OH}$ 5.20 Hz and 4.20 Hz, 6'-OH), 4.50 (m, 2H, 6-OH and 4'-OH), 4.24 (d, 1H, $J_{1',2'}$ 6.87 Hz, H-1'), 4.03 and 3.92 (2 dd, each 1H, $J_{gem}$ 13.00 Hz, CH$_2$Ph), 3.96 and 3.78 (2 dd, each 1H, $J_{gem}$ 13.00 Hz, CH$_2$Ph), 3.80 (d, 1H, $J_{1,2}$ 8.98 Hz, H-1), 3.78 and 3.63 (2 m, each 1H, H-6), 3.652 (m, 2H, H-6'), 3.60 (m, 1H, H-4'), 3.40 (m, 1H, H-3), 3.28 (m, 1H, H-2'), 2.95 and 2.00 (2 bs, each 1H, NH), 2.37 (dd, 1H, H-2).

13C NMR (DMSO d6) δ: 141.39 and 141.71 (aromatic), 103.72 (C-1'), 89.37 (C-1), 81.65 (C-4), 75.62 (C-2), 75.28 and 73.00 (C-5 and C-5'), 75.28 (C-3), 70.40 (C-3'), 67.94 (C-4'), 62.68 (C-2), 60.79 and 60.21 (C$_{1-6}$ and C-6'), 52.37 and 48.11 (CH$_2$Ph).

2. Preparation of 1,2-dideoxy-1,2-di-ρ-methylbenzylamino lactose

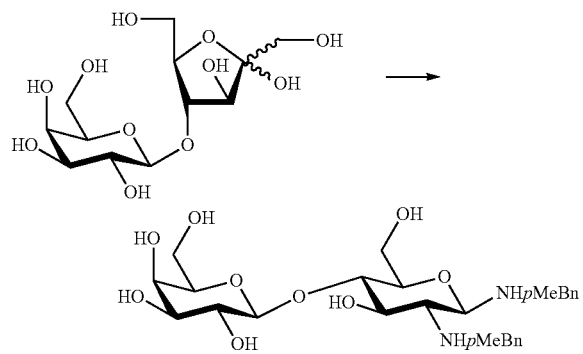

1st experiment: Lactulose (50 g) and ρ-methylbenzylamine hydrochloride (1 g) were added to ρ-methylbenzylamine (100 mL) at 0° C. and the white suspension stirred at 0° C. for 4 days. Then acetone (300 mL) was added to the mixture followed by the addition of hexane (300 mL). The mixture was shaken then the upper phase discarded. To the lower phase again acetone (300 mL) and hexane (300 mL) were added and extracted. The phases were separated and the extraction repeated once with the same amounts of solvents. Finally, the lower phase was concentrated obtaining the crude reaction mixture. The product was crystallized after addition of methanol (100 mL). The white crystals were filtered, washed and dried. Yield: 27 g beta isomer. The mother liquor contains a mixture of alpha and beta anomers.

2nd experiment: Lactulose (50 g) and $P_2O_5$ (100 mg) were added to ρ-methylbenzylamine (100 mL) at 0° C. and the white suspension stirred at 40° C. for 4 days. Then acetone (100 mL) was added to the mixture followed by the addition of hexane (200 mL). The mixture was shaken then the upper phase discarded. To the lower phase again acetone (100 mL) and hexane (200 mL) were added and extracted. The phases were separated and the extraction repeated once with the same amounts of solvents. Finally, the lower phase was concentrated obtaining the crude reaction mixture. The product was crystallized after addition of methanol (50 mL). The white crystals were filtered, washed and dried. Yield: 29 g beta isomer.

3rd experiment: Lactulose (50 g) and $ZnCl_2$ (500 mg) were added to ρ-methylbenzylamine (100 mL) at 0° C. and the white suspension stirred at 40° C. for 4 days. Then acetone (100 mL) was added to the mixture followed by the addition of hexane (200 mL). The mixture was shaken then the upper phase discarded. To the lower phase again acetone (100 mL) and hexane (200 mL) were added and extracted. The phases were separated and the extraction repeated once with the same amounts of solvents. Finally, the lower phase was concentrated obtaining the crude reaction mixture. The product was crystallized after addition of methanol (100 mL). The white crystals were filtered, washed and dried. Yield: 27 g beta isomer.

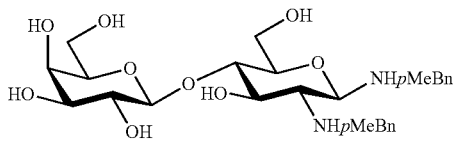

1H NMR. (DMSO d6) δ: 7.20-7.02 (m, 8H, aromatic), 5.14, 5.08, 4.80, 4.69, 4.63 and 4.52 (6 bs, each 1H, 6×OH), 4.18 (d, 1H, $J_{1',2'}$ 7.87 Hz, H-1'), 3.93 and 3.85 (2 m, each 1H, $J_{gem}$ 12.97 Hz, $CH_2Ph$), 3.88 and 3.70 (2 m, each 1H, $CH_2Ph$), 3.78 (d, 1H, $J_{1,2}$ 8.98 Hz, H-1), 2.85 and 2.48 (2 bs, each 1H, NH), 2.34 (dd, 1H, H-2).

13C NMR (DMSO d6) δ: 104.53 (C-1'), 82.29 (C-1'), 81.96, 75.99, 75.98, 75.95, 73.66, 71.01, and 68.68 (C-3, C-4, C-5, C-2', C-3', C-4' and C-5'), 62.05 and 61.05 (C-6 and C-6'), 52.76 and 48.46 ($CH_2Ph$).

3. Preparation of 1,2-dideoxy-1,2-di-ρ-methoxybenzylamino lactose

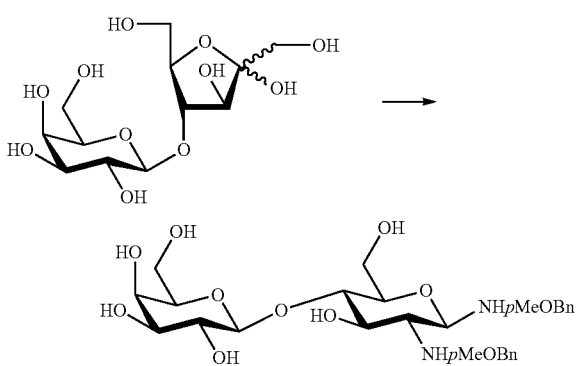

1st experiment: Lactulose (50 g) and $P_2O_5$ (100 mg) were added to ρ-methoxybenzylamine (100 mL) at 0° C. and the white suspension stirred at 40° C. for 4 days. Then acetone (100 mL) was added to the mixture followed by the addition of hexane (200 mL). The mixture was shaken then the upper phase discarded. To the lower phase again acetone (100 mL) and hexane (200 mL) were added and extracted. The phases were separated and the extraction repeated once with the same amounts of solvents. Finally, the lower phase was concentrated obtaining the crude reaction mixture. The product was crystallized after addition of methanol (50 mL). The white crystals were filtered, washed and dried. Yield: 23 g.

2nd experiment: Lactulose (50 g) and Amberlite IR 120 ($H^+$) (100 mg) were added to ρ-methoxybenzylamine (100 mL) at 0° C. and the white suspension stirred at 40° C. for 4 days. Then acetone (100 mL) was added to the mixture followed by the addition of hexane (200 mL). The mixture was shaken then the upper phase discarded. To the lower phase again acetone (100 mL) and hexane (200 mL) were added and extracted. The phases were separated and the extraction repeated once with the same amounts of solvents. Finally, the lower phase was concentrated obtaining the crude reaction mixture. The product was crystallized after addition of methanol (100 mL). The white crystals were filtered, washed and dried. Yield: 22 g.

4. Preparation of 1,2-dideoxy-1,2-di-ρ-chlorobenzylamino lactose

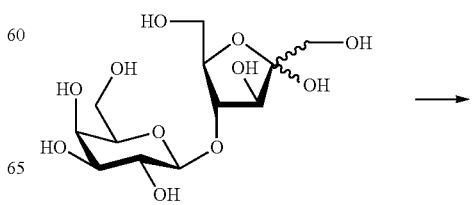

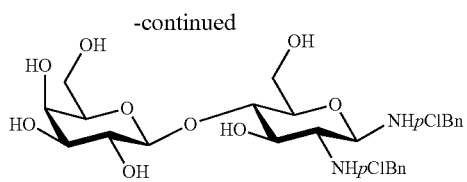

1$^{st}$ experiment: Lactulose (50 g) and P$_2$O$_5$ (100 mg) were added to ρ-chlorobenzylamine (100 mL) at 0° C. and the white suspension stirred at 40° C. for 4 days. Then acetone (100 mL) was added to the mixture followed by the addition of hexane (200 mL). The mixture was shaken then the upper phase discarded. To the lower phase again acetone (100 mL) and hexane were (200 mL) added and extracted. The phases were separated and the extraction repeated once with the same amounts of solvents. Finally, the lower phase was concentrated obtaining the crude reaction mixture. The product was crystallized after addition of acetone (50 mL). The white crystals were filtered, washed and dried. Yield: 29 g.

2$^{nd}$ experiment: Lactulose (50 g) and Amberlite IR 120 (H$^+$) (100 mg) added to ρ-chlorobenzylamine (100 mL) at 0° C. and the white suspension stirred at 40° C. for 4 days. Then acetone (100 mL) was added to the mixture and the product was isolated as a white crystal. The white crystals were filtered, washed and dried. Yield: 31 g.

5. Preparation of 1,2-dideoxy-1,2-di-benzylamino maltose

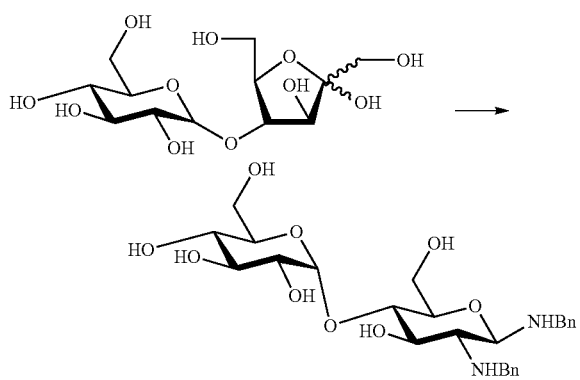

1$^{st}$ experiment: Maltulose (5 g) and P$_2$O$_5$ (10 mg) were added to benzylamine (10 mL) at 0° C. and the white suspension stirred at 40° C. for 4 days. Then acetone (10 mL) was added to the mixture followed by the addition of hexane (20 mL). The mixture was shaken then the upper phase discarded. To the lower phase again acetone (10 mL) and hexane (20 mL) were added and extracted. The phases were separated and the extraction repeated once with the same amounts of solvents. Finally, the lower phase was concentrated obtaining the crude reaction mixture. The product was crystallized after addition of methanol (20 mL). The white crystals were filtered, washed and dried. Yield: 2.4 g.

2$^{nd}$ experiment: Maltulose (5 g) and Amberlite IR 120 (H$^+$) (50 mg) were added to benzylamine (10 mL) at 0° C. and the white suspension stirred at 40° C. for 4 days. Then acetone (10 mL) was added to the mixture followed by the addition of hexane (20 mL). The mixture was shaken then the upper phase discarded. To the lower phase again acetone (10 mL) and hexane (20 mL) were added and extracted. The phases were separated and the extraction repeated once with the same amounts of solvents. Finally, the lower phase was concentrated obtaining the crude reaction mixture. The product was crystallized after addition of methanol (20 mL). The white crystals were filtered, washed and dried. Yield: 2.6 g.

6. Preparation of 1,2-dideoxy-1,2-di-ρ-methylbenzylamino maltose

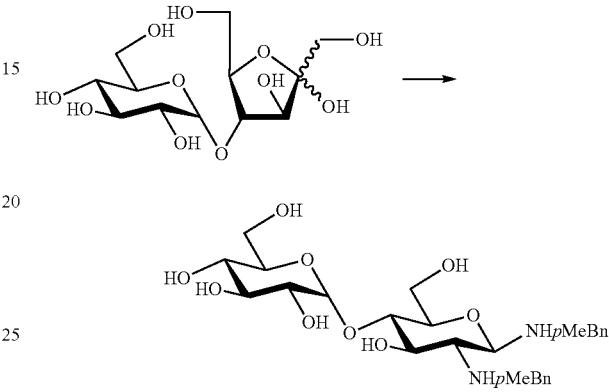

1$^{st}$ experiment: Maltulose (5 g) and P$_2$O$_5$ (10 mg) were added to ρ-methylbenzylamine (10 mL) at 0° C. and the white suspension stirred at 40° C. for 4 days. Then acetone (10 mL) was added to the mixture followed by the addition of hexane (20 mL). The mixture was shaken then the upper phase discarded. To the lower phase again acetone (10 mL) and hexane (20 mL) were added and extracted. The phases were separated and the extraction repeated once with the same amounts of solvents. Finally, the lower phase was concentrated obtaining the crude reaction mixture. The product was crystallized after addition of acetone (20 mL). The white crystals were filtered, washed and dried. Yield: 2.1 g.

2$^{nd}$ experiment: Maltulose (5 g) and ZnCl$_2$ (10 mg) were added to ρ-methylbenzylamine (10 mL) at 0° C. and the white suspension stirred at 40° C. for 4 days. Then acetone (10 mL) was added to the mixture followed by the addition of hexane (20 mL). The mixture was shaken then the upper phase discarded. To the lower phase again acetone (10 mL) and hexane (20 mL) were added and extracted. The phases were separated and the extraction repeated once with the same amounts of solvents. Finally, the lower phase was concentrated obtaining the crude reaction mixture. The product was crystallized after addition of acetone (20 mL). The white crystals were filtered, washed and dried. Yield: 1.9 g.

7. Preparation of 1,2-dideoxy-1,2-di-ρ-methoxybenzylamino maltose

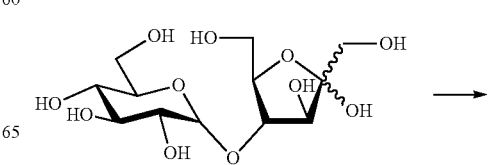

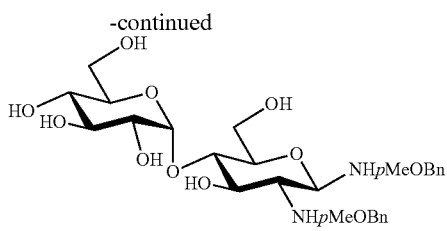

Maltulose (5 g) and P$_2$O$_5$ (10 mg) were added to ρ-methylbenzylamine (10 mL) at 0° C. and the white suspension stirred at 40° C. for 4 days. Then acetone (10 mL) was added to the mixture followed by the addition of hexane (20 mL). The mixture was shaken then the upper phase discarded. To the lower phase again acetone (10 mL) and hexane (20 mL) were added and extracted. The phases were separated and the extraction repeated once with the same amounts of solvents. Finally, the lower phase was concentrated obtaining the crude reaction mixture. The product was crystallized after addition of acetone (20 mL). The white crystals were filtered, washed and dried. Yield: 3.1 g.

8. Preparation of 1,2-dideoxy-1,2-di-ρ-chlorobenzylamino maltose

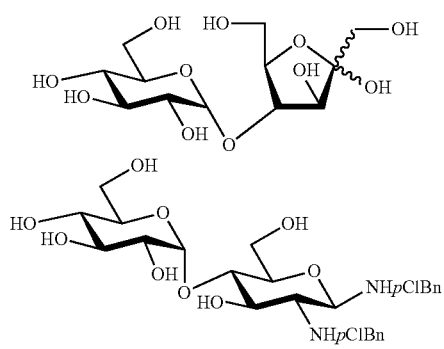

Maltulose (5 g) and P$_2$O$_5$ (10 mg) were added to ρ-chlorobenzylamine (10 mL) at 0° C. and the white suspension stirred at 40° C. for 4 days. Then acetone (10 mL) was added to the mixture followed by the addition of hexane (20 mL). The mixture was shaken then the upper phase discarded. To the lower phase again acetone (10 mL) and hexane (20 mL) were added and extracted. The phases were separated and the extraction repeated once with the same amounts of solvents. Finally, the lower phase was concentrated obtaining the crude reaction mixture. The product was crystallized after addition of acetone (20 mL). The white crystals were filtered, washed and dried. Yield: 2.9 g.

9. Preparation of 1,2-dideoxy-1,2-di-benzylamino isomaltose

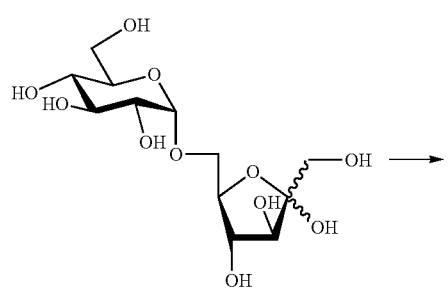

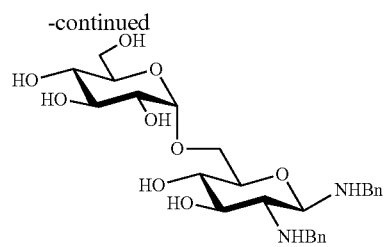

1$^{st}$ experiment: Palatinose (5 g) and P$_2$O$_5$ (10 mg) added to benzylamine (10 mL) at 0° C. and the white suspension stirred at 40° C. for 4 days. Then acetone (10 mL) was added to the mixture followed by the addition of hexane (20 mL). The mixture was shaken then the upper phase discarded. To the lower phase again acetone (10 mL) and hexane (20 mL) were added and extracted. The phases were separated and the extraction repeated once with the same amounts of solvents. Finally, the lower phase was concentrated obtaining the crude reaction mixture. The product was precipitated after addition of diethyl ether (50 mL). The yellow powder was filtered, washed and dried. Yield: 5.3 g.

2$^{nd}$ experiment: Palatinose (5 g) and AlCl$_3$ (10 mg) were added to benzylamine (10 mL) at 0° C. and the white suspension stirred at 40° C. for 4 days. Then acetone (10 mL) was added to the mixture followed by the addition of hexane (20 mL). The mixture was shaken then the upper phase discarded. To the lower phase again acetone (10 mL) and hexane (20 mL) were added and extracted. The phases were separated and the extraction repeated once with the same amounts of solvents. Finally, the lower phase was concentrated obtaining the crude reaction mixture. The product was precipitated after addition of diethyl ether (50 mL). The yellow powder was filtered, washed and dried. Yield: 5.0 g.

10. Preparation of 1,2-dideoxy-1,2-di-ρ-methylbenzylamino isomaltose

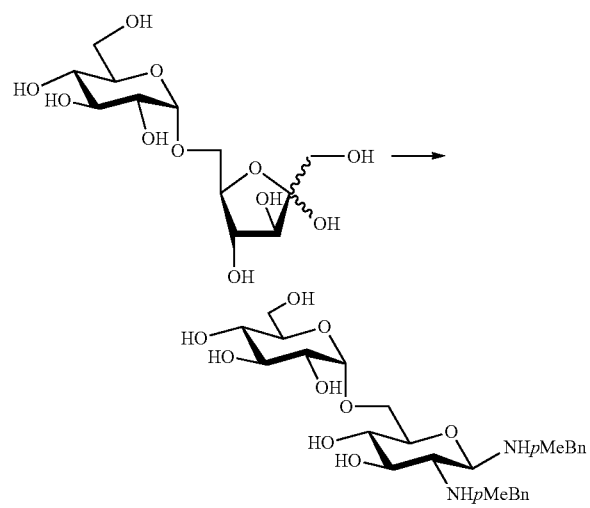

Palatinose (5 g) and P$_2$O$_5$ (10 mg) were added to ρ-methylbenzylamine (10 mL) at 0° C. and the white suspension stirred at 40° C. for 4 days. Then acetone (10 mL) was added to the mixture followed by the addition of hexane (20 mL). The mixture was shaken then the upper phase discarded. To the lower phase again acetone (10 mL) and hexane (20 mL) were added and extracted. The phases were separated and the extraction repeated once with the same amounts of solvents. Finally, the lower phase was concentrated obtaining the crude reaction mixture. The product was precipitated after addition of diethyl ether (50 mL). The white powder was filtered, washed and dried. Yield: 5.5 g.

11. Preparation of 1,2-dideoxy-1,2-di-ρ-methoxybenzylamino isomaltose

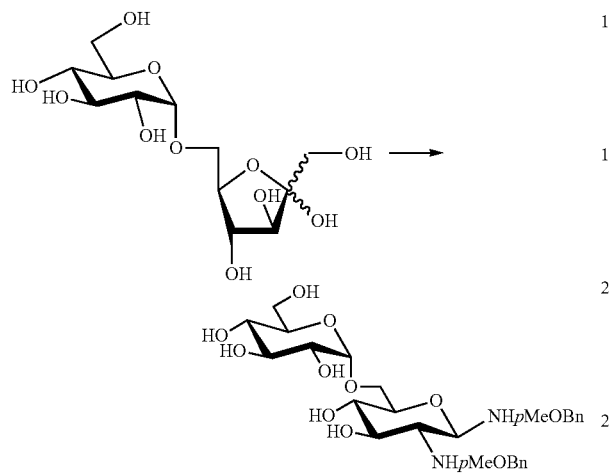

Palatinose (5 g) and P$_2$O$_5$ (10 mg) were added to ρ-methoxybenzylamine (10 mL) at 0° C. and the white suspension stirred at 40° C. for 4 days. Then acetone (10 mL) was added to the mixture followed by the addition of hexane (20 mL). The mixture was shaken then the upper phase discarded. To the lower phase again acetone (10 mL) and hexane (20 mL) were added and extracted. The phases were separated and the extraction repeated once with the same amounts of solvents. Finally, the lower phase was concentrated obtaining the crude reaction mixture. The product was precipitated after addition of diethyl ether (100 mL). The white powder was filtered, washed and dried. Yield: 6.1 g.

12. Preparation of 1,2-dideoxy-1,2-di-ρ-chlorobenzylamino isomaltose

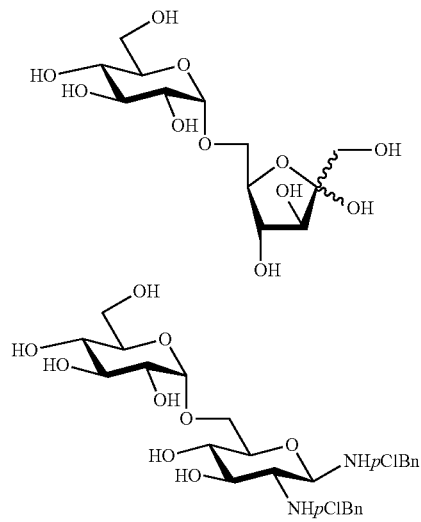

Palatinose (5 g) and P$_2$O$_5$ (10 mg) were added to ρ-chlorobenzylamine (10 mL) at 0° C. and the white suspension stirred at 40° C. for 4 days. Then acetone (10 mL) was added to the mixture followed by the addition of hexane (20 mL). The mixture was shaken then the upper phase discarded. To the lower phase again acetone (10 mL) and hexane (20 mL) were added and extracted. The phases were separated and the extraction repeated once with the same amounts of solvents. Finally, the lower phase was concentrated obtaining the crude reaction mixture. The product was precipitated after addition of diethyl ether (50 mL). The yellow powder was filtered, washed and dried. Yield: 5.9 g.

13. Preparation of 1,2-dideoxy-1,2-di-benzylamino nigerose

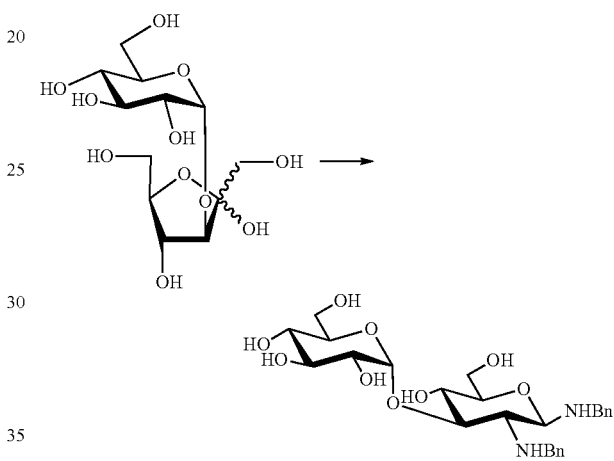

Turanose (5 g) and Amberlite IR 120 (H$^+$) (50 mg) were added to benzylamine (10 mL) at 0° C. and the white suspension stirred at 40° C. for 4 days. Then acetone (10 mL) was added to the mixture followed by the addition of hexane (20 mL). The mixture was shaken then the upper phase discarded. To the lower phase again acetone (10 mL) and hexane (20 mL) were added and extracted. The phases were separated and the extraction repeated once with the same amounts of solvents. Finally, the lower phase was concentrated obtaining the crude reaction mixture. The product was precipitated after addition of diethyl ether (50 mL). The yellow powder was filtered, washed and dried. Yield: 6.1 g.

14. Preparation of 1,2-dideoxy-1,2-di-ρ-methylbenzylamino nigerose

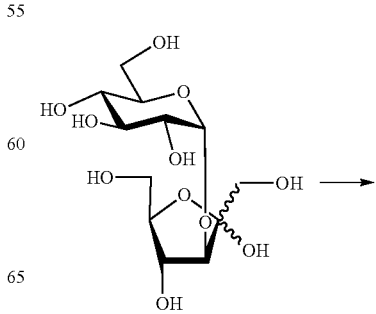

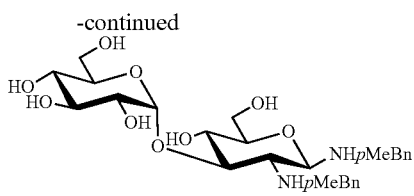

Turanose (5 g) and P₂O₅ (10 mg) were added to ρ-methylbenzylamine (10 mL) at 0° C. and the white suspension stirred at 40° C. for 4 days. Then acetone (10 mL) was added to the mixture followed by the addition of hexane (20 mL). The mixture was shaken then the upper phase discarded. To the lower phase again acetone (10 mL) and hexane (20 mL) were added and extracted. The phases were separated and the extraction repeated once with the same amounts of solvents. Finally, the lower phase was concentrated obtaining the crude reaction mixture. The product was precipitated after addition of diethyl ether (100 mL). The yellow powder was filtered, washed and dried. Yield: 5.8 g.

15. Preparation of 1,2-dideoxy-1,2-di-ρ-methoxybenzylamino nigerose

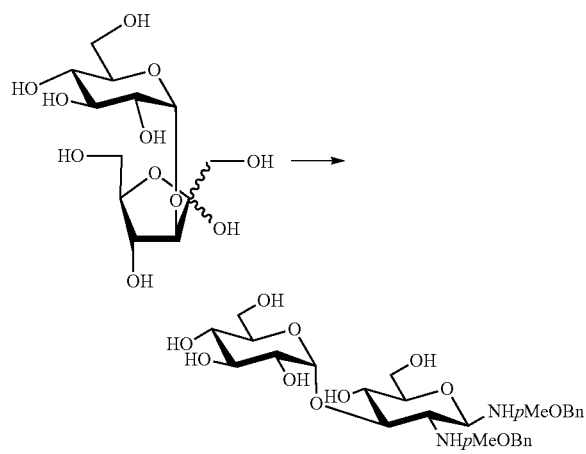

Turanose (5 g) and Amberlite IR 120 (H⁺) (50 mg) were added to ρ-methoxybenzylamine (10 mL) at 0° C. and the white suspension stirred at 40° C. for 4 days. Then acetone (10 mL) was added to the mixture followed by the addition of hexane (20 mL). The mixture was shaken then the upper phase discarded. To the lower phase again acetone (10 mL) and hexane (20 mL) were added and extracted. The phases were separated and the extraction repeated once with the same amounts of solvents. Finally, the lower phase was concentrated obtaining the crude reaction mixture. The product was precipitated after addition of MTBE (tert-butylmethyl ether) (100 mL). The yellow powder was filtered, washed and dried. Yield: 6.5 g.

16. Preparation of 1,2-dideoxy-1,2-di-ρ-chlorobenzylamino nigerose

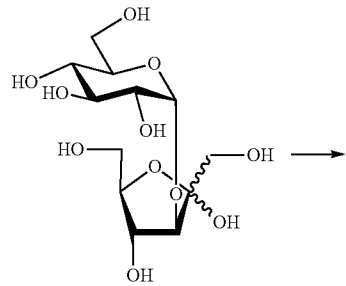

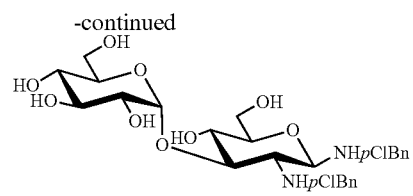

Turanose (5 g) and P₂O₅ (10 mg) were added to ρ-chlorobenzylamine (10 mL) at 0° C. and the white suspension stirred at 40° C. for 4 days. Then acetone (10 mL) was added to the mixture followed by the addition of hexane (20 mL). The mixture was shaken then the upper phase discarded. To the lower phase again acetone (10 mL) and hexane (20 mL) were added and extracted. The phases were separated and the extraction repeated once with the same amounts of solvents. Finally, the lower phase was concentrated obtaining the crude reaction mixture. The product was precipitated after addition of tert-butylmethyl ether (MTBE) (100 mL). The white powder was filtered, washed and dried. Yield: 5.9 g.

17. Preparation of 2-deoxy-2-benzylamino lactose

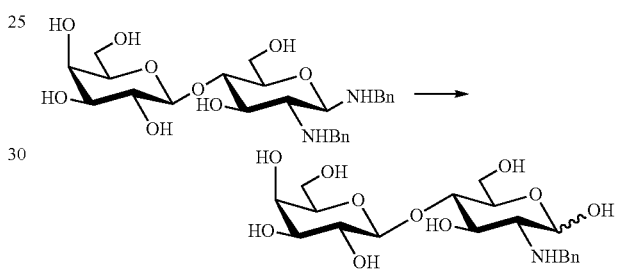

1,2-dideoxy-1,2-di-benzylamino lactose (20 g) was added to a mixture of methanol (180 mL) and water (20 mL). The suspension was stirred for 7 days, then concentrated to dryness. The residue was dissolved in methanol (20 mL) and dropped into tert-butylmethyl ether (150 mL). The white powder was filtered, washed with tert-butylmethyl ether (30 mL) and dried obtaining the product. Yield 16.2 g

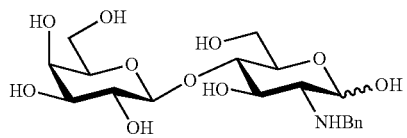

1H NMR. (D₂O) δ: 7.30 (m, 5H, aromatic), 5.33 (d, 1H, $J_{1,2}$ 3.57 Hz, H-1 α), 4.90 (d, 1H, $J_{1,2}$ 8.40 Hz, H-1 β), 4.23 (d, 1H, $J_{1',2'}$ 7.69 Hz, H-1' α), 4.20 (d, 1H, $J_{1',2'}$ 7.43 Hz, H-1' β), 3.36 and 3.33 (m, 2H, H-2' α and β), 3.10 (dd, 1H, H-2 α), 2.83 (m, 1H, H-2 β).

18. Preparation of 2-deoxy-2-benzylamino lactose in HCl salt form

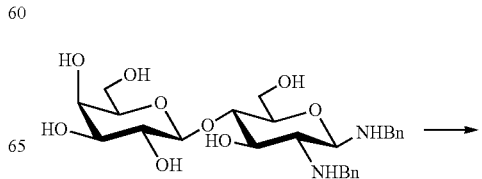

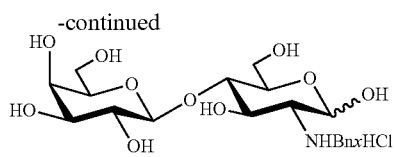

1,2-dideoxy-1,2-di-benzylamino lactose (20 g) was added to a mixture of methanol (180 mL) and water (20 mL). Then the pH of the mixture was adjusted to 1 by the addition of 10% HCl (approx. 35 mL). The suspension was stirred for 30 min, then concentrated to dryness. The residue was dissolved in methanol (30 mL) and dropped into tert-butylmethyl ether (150 mL). The white powder was filtered, washed with tert-butylmethyl ether (30 mL) and dried obtaining the salt. Yield: 16.7 g.

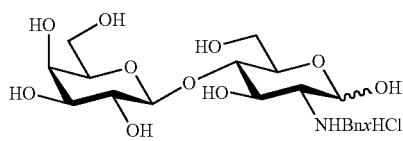

1H NMR. (D$_2$O) δ: 7.30 (m, 5H, aromatic), 5.33 (d, 1H, J$_{1,2}$ 3.57 Hz, H-1 α), 4.90 (d, 1H, J$_{1,2}$ 8.40 Hz, H-1 β), 4.23 (d, 1H, J$_{1',2'}$ 7.69 Hz, H-1' α), 4.20 (d, 1H, J$_{1',2'}$ 7.43 Hz, H-1' β), 3.36 and 3.33 (m, 2H, H-2' α and β), 3.10 (dd, 1H, H-2 α), 2.83 (m, 1H, H-2 β).

19. Preparation of 2-deoxy-2-amino lactose in HCl salt form (lactosamine hydrochloride)

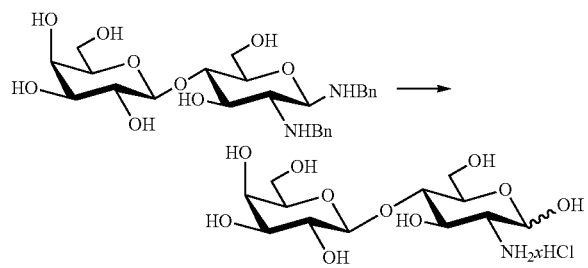

1,2-dideoxy-1,2-di-benzylamino lactose (20 g) was added to the mixture of methanol (180 mL) and water (20 mL). Then the pH of the mixture was adjusted to 1 by the addition of 10% HCl (approx. 35 mL). The suspension was stirred for 30 min, then Pd/C was added (1 g) in water (10 mL) and the mixture stirred under H$_2$ atmosphere (20 bar) for 2 days. Then the mixture was filtered and the filtrate concentrated. The product was isolated after refluxing the residue in ethanol (96%, 50 mL) as a white solid. Yield 13.8 g.

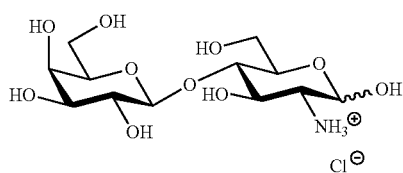

1H NMR. (D$_2$O) δ: 5.23 (d, 1H, J$_{1,2}$ 3.10 Hz, H-1 α), 4.75 (d, 1H, J$_{1,2}$ 8.43 Hz, H-1 β), 4.25 (d, 1H, J$_{1',2'}$ 7.25 Hz, H-1' α and β) 3.34 (m, 1H, H-2' α and β), 3.14 (dd, 1H, H-2 α), 2.83 (m, 1H, H-2 β).

13C NMR (D$_2$O) δ: 103.13 (C-1' β), 103.08 (C-1' α), 92.67 (C-1 α), 88.99 (C-1 β), 78.08, 75.51, 72.54, 71.05, 70.38, 68.62, 68.45, 61.23, 59.74 and 54.13 (C-2, 3, 4, 5, 6, C-2', 3', 4', 5', 6', all α).

20. Preparation of 2-deoxy-2-amino lactose in HCl salt form (lactosamine hydrochloride)

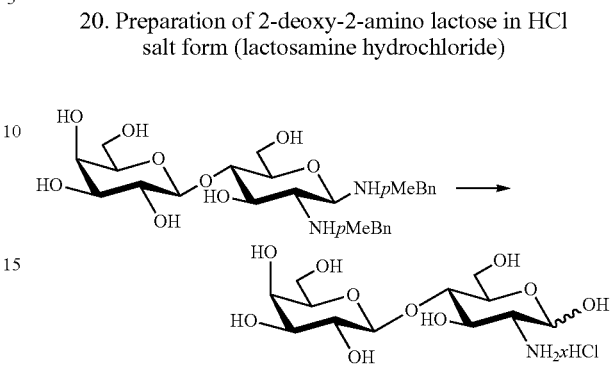

1,2-dideoxy-1,2-di-ρ-methylbenzylamino lactose (5 g) was added to a mixture of methanol (30 mL) and water (3 mL). Then the pH of the mixture was adjusted to 1 by the addition of 10% HCl (approx. 2.8 mL). The suspension was stirred for 30 min, then Pd/C added (100 mg) in water (2 mL) and the mixture stirred under H$_2$ atmosphere (20 bar) for 2 days. Then the mixture was filtered and the filtrate concentrated. The product was isolated after refluxing the residue in ethanol (96%, 50 mL) as a white solid. Yield 2.8 g NMR data see above in the text.

21. Preparation of 2-deoxy-2-amino lactose in HCl salt form (lactosamine hydrochloride)

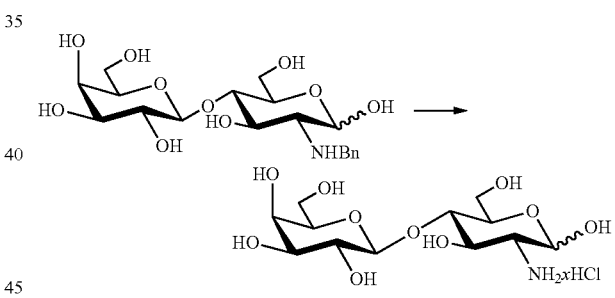

2-deoxy-2-benzylamino lactose (10 g) was added to a mixture of methanol (100 mL) and water (20 mL). Then the pH of the mixture was adjusted to 1 by the addition of 10% HCl (approx. 8 mL), and then Pd/C (200 mg) in water (5 mL) was added. The mixture was stirred under H$_2$ atmosphere (20 bar) for 2 days. Then the mixture was filtered and the filtrate concentrated. The product was isolated after refluxing the residue in ethanol (96%, 25 mL) as a white solid Yield: 6.8 g.

NMR data see above in the text.

22. Preparation of 2-deoxy-2-amino lactose in HCl salt form (lactosamine hydrochloride)

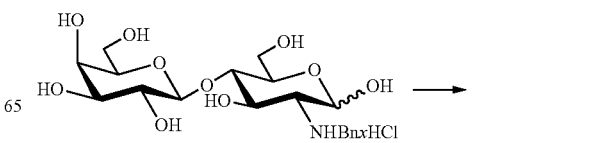

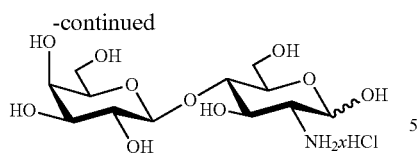

2-deoxy-2-benzylamino lactose hydrochloride salt (5 g) was added to a mixture of methanol (30 mL) and water (3 mL). Then Pd/C (100 mg) in water (3 mL) was added to the mixture which was then stirred under $H_2$ atmosphere (20 bar) for 2 days. Then the mixture was filtered and the filtrate concentrated. The product was isolated after refluxing the residue in ethanol (96%, 15 mL) as a white solid Yield: 3.1 g.

NMR data see above in the text.

REFERENCES

1. L. C. Maillard, *Compt. rend.* 1912, 154, 66-68.
2. M. Amadori *Lincei,* 1925, 2 337-42.
3. a) E. Fischer. *Ber.* 1884, 17, 579-584, b) E. Fischer *Ber.* 1886, 19, 1920-1924.
4. K. Heyns, W. Koch. *Z. Naturforsch.* 1952, 7b, 486-488.
5. a) J. F. Carson, *J. Am. Chem. Soc.* 1955, 77, 1881-1884. b) J. F. Carson, *J. Am. Chem. Soc.* 1955, 77, 5957-5960. c) J. F. Carson, *J. Am. Chem. Soc.* 1956, 78, 3728-3731. c) K. Heyns, K.-H. Meinecke, *Chem. Ber.* 1953, 86, 1453-1462. d) K. Heyns, K.-W. Pflughaupt, D. Miiller, *Chem. Ber.* 1968, 101, 2807-2814. e) K. Heyns, H. Paulsen, H. Breuer, *Angew. Chem.* 1956, 68, 334-335. f) K. Heyns, H. Breuer, H. Paulsen, *Chem. Ber.* 1957, 90, 1374-1386. g) K. Heyns, H. Paulsen, H. Breuer, *Chem. Ber.* 1958, 91, 2750-2762. h) K. Heyns, H. Noack, *Chem. Ber.* 1964, 97, 415-418. i) K. Heyns, R. Eichstedt, K. H. Meinecke, *Chem. Ber.* 1955, 88, 1551-1555. j) K. Heyns, H. Paulsen, R. Eichstedt, M. Rolle, *Chem. Ber.* 1957, 90, 2039-2049. k) K. Heyns, K.-W. Pflughaupt, H. Paulsen, *Chem. Ber.* 1968, 101, 2800-2806. l) K. Heyns, W. BeilfuR, *Chem. Ber.* 1970, 103, 2873-2876.
6. P. S. Piispannen, T Norin, *J. Org. Chem.* 2003, 68, 628-630.
7. T. M. Wrodnigg, A. E. Stütz *Angew. Chem. Int. Ed. Engl.* 1999, 38(6), 827-828. A. E. Stütz, Gy. Dékány, B. Eder, C. Illaszewicz, T. M. Wrodnigg *J. Carbohydr. Chem.* 2002, 22(5), 253-265.

The invention claimed is:

1. A 1,2-dideoxy-1,2-diamino disaccharide in its free base, salt or metal-complex form which is a 1→4 linked disaccharide as shown in General Formula 2, a 1>6 linked disaccharide as shown in General Formula 3, or a 1→3 linked disaccharide as shown in General Formula 4

General Formula 2

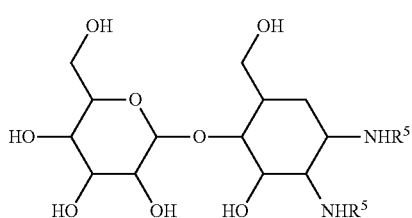

General Formula 3

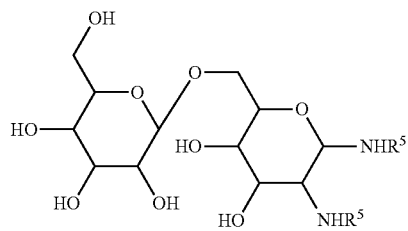

General Formula 4

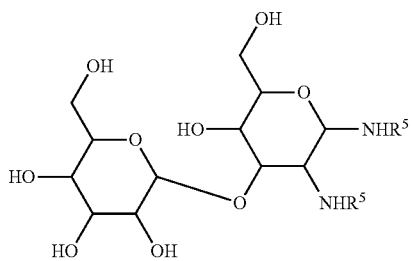

wherein $R^5$ is selected from the group consisting of: optionally substituted benzyl, optionally substituted benzhydryl, optionally substituted trityl, and optionally substituted naphthylmethyl.

2. A medicament comprising a 1,2-dideoxy-1,2-diamino disaccharide as defined in claim 1, formulated for pharmaceutical administration.

3. A food product comprising a 1,2-dideoxy-1,2-diamino disaccharide as claimed in claim 1.

4. The 1,2-dideoxy-1,2-diamino disaccharide of claim 1, wherein $R^5$ is an optionally substituted benzyl group.

5. The 1,2-dideoxy-1,2-diamino disaccharide of claim 1, wherein $R^5$ is a benzyl group.

6. The 1,2-dideoxy-1,2-diamino disaccharide of claim 1, which is a 1→4 linked disaccharide as shown in General Formula 2.

7. The 1,2-dideoxy-1,2-diamino disaccharide of claim 6, which is a 1,2-dideoxy-1,2-diamino lactose derivative.

8. A method for the preparation of a 1,2-dideoxy-1,2-diamino disaccharide, said method comprising reacting disaccharide ketose as shown in any one of Formulas 2, 3, and 4 shown below

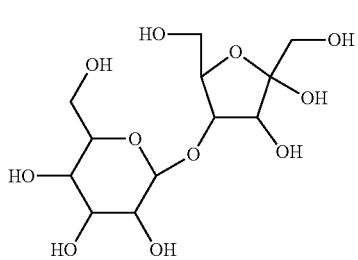

3

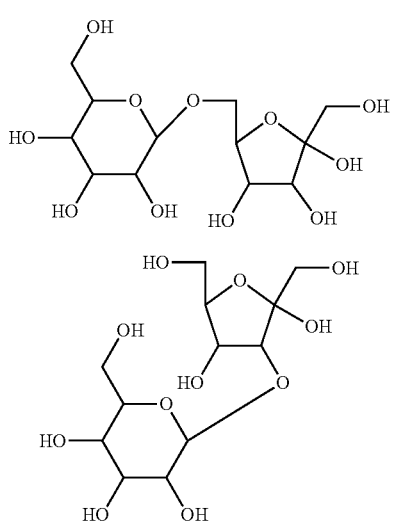

4

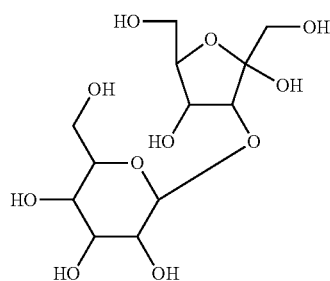

with an amine selected from the group consisting of: optionally substituted benzylamine, optionally substituted benzhydrylamine, optionally substituted tritylamine, and optionally substituted naphthylmethylamine,
wherein the reaction is catalyzed by a compound selected from: an organic or an inorganic protic acid either in soluble or insoluble form; a Lewis acid; a polymer bound acid; a zeolite; an oxide; the acid addition salt of the amine.

9. A method of producing a 2 amino-2-deoxy disaccharide represented by Formulas 5, 6, or 7

Formula 5

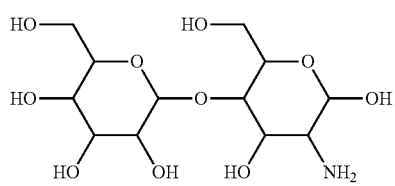

Formula 6

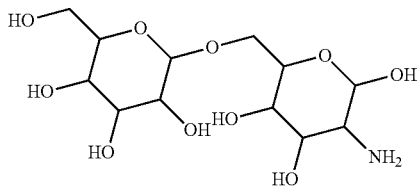

Formula 7

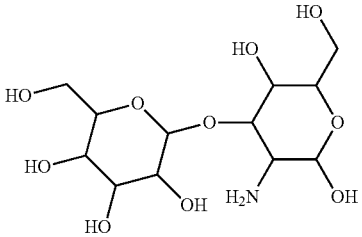

in a free base, salt or metal-complexed form, comprising carrying out the method of claim 8 to obtain a 1,2-dideoxy-1,2-diamino disaccharide, and converting the 1,2-dideoxy-1,2-diamino disaccharide into the 2-amino-2-deoxy disaccharide.

10. The method according to claim 8, in which the amine is optionally substituted benzylamine.

11. The method according to claim 10, in which the amine is benzylamine.

12. The method according to claim 8, in which the 1,2-dideoxy-1,2-diamino disaccharide is as shown in General Formula 2, and in which the disaccharide ketose is as shown in Formula 2.

13. The method according to claim 12, in which the disaccharide ketose is lactulose.

14. The method according to claim 8, in which the reaction is catalyzed by the acid addition salt of the amine.

15. The method according to claim 9, wherein the 2-amino-2-deoxy disaccharide is as shown in Formula 5.

16. The method according to claim 9, in which the 2-amino-2-deoxy disaccharide is lactosamine in a free base, salt or metal complexed form.

* * * * *